United States Patent
Miyasa et al.

(10) Patent No.: US 9,396,576 B2
(45) Date of Patent: Jul. 19, 2016

(54) METHOD AND APPARATUS FOR ESTIMATING THE THREE-DIMENSIONAL SHAPE OF AN OBJECT

(71) Applicant: CANON KABUSHIKI KAISHA, Tokyo (JP)

(72) Inventors: Kazuhiro Miyasa, Yokohama (JP); Kiyohide Satoh, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/452,649

(22) Filed: Aug. 6, 2014

(65) Prior Publication Data

US 2015/0043800 A1 Feb. 12, 2015

(30) Foreign Application Priority Data

Aug. 9, 2013 (JP) .................................. 2013-166992

(51) Int. Cl.
*G06T 15/00* (2011.01)
*G06T 7/00* (2006.01)
*G06T 17/00* (2006.01)
*A61B 5/00* (2006.01)
*A61B 5/055* (2006.01)

(52) U.S. Cl.
CPC .............. *G06T 15/00* (2013.01); *A61B 5/4312* (2013.01); *G06T 7/0028* (2013.01); *G06T 17/00* (2013.01); *A61B 5/0095* (2013.01); *A61B 5/055* (2013.01); *G06T 2200/04* (2013.01); *G06T 2207/10048* (2013.01); *G06T 2207/10072* (2013.01); *G06T 2207/10088* (2013.01); *G06T 2207/30068* (2013.01); *G06T 2210/41* (2013.01)

(58) Field of Classification Search
None
See application file for complete search history.

(56) References Cited

U.S. PATENT DOCUMENTS

2010/0087733 A1* 4/2010 Nakajima ............ A61B 5/0073 600/437

FOREIGN PATENT DOCUMENTS

JP 2008235504 A 10/2008
JP 2010088627 A 4/2010

OTHER PUBLICATIONS

Dehghani, Hamid, et al. "Breast deformation modelling for image reconstruction in near infrared optical tomography." Physics in medicine and biology 49.7 (2004): 1131.*
Lee, et al., "Breast X-ray and MR Image Fusion Using Finite Element Modeling", Proc. Workshop on Breast Image Analysis in conjunction with MICCAI 2011, pp. 129-136, 2011.
Iwashita, et al., "2D-3D Registration Using 2D Distance Maps" in Meeting on Image Recognition and Understanding 2005 (MIRU2005), pp. 1-8.
C. Tanner, et al., "Breast Shapes on Real and Simulated Mammograms", Proc. Int. Workshop on Digital Mammography 2010 (IWDM 2010), LNCS 6136, pp. 540-547, 2010.

* cited by examiner

*Primary Examiner* — Nirav G Patel
(74) *Attorney, Agent, or Firm* — Carter, DeLuca, Farrell & Schmidt, LLP

(57) ABSTRACT

A contact region between an object and a holding member is acquired based on the image obtained by imaging the object in a held state in which the object is held by the holding member. The three-dimensional shape of the object in a held state is estimated based on the contact region.

28 Claims, 16 Drawing Sheets

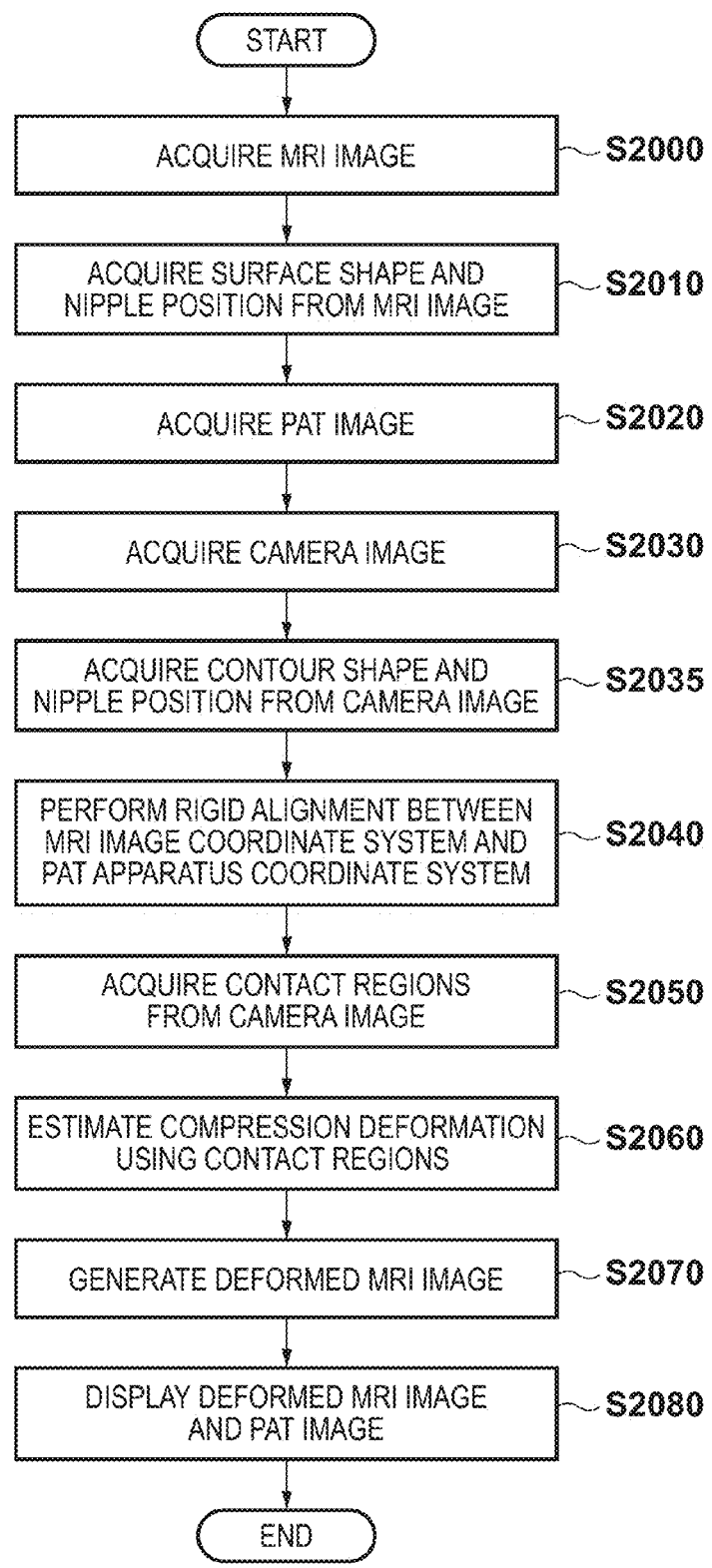

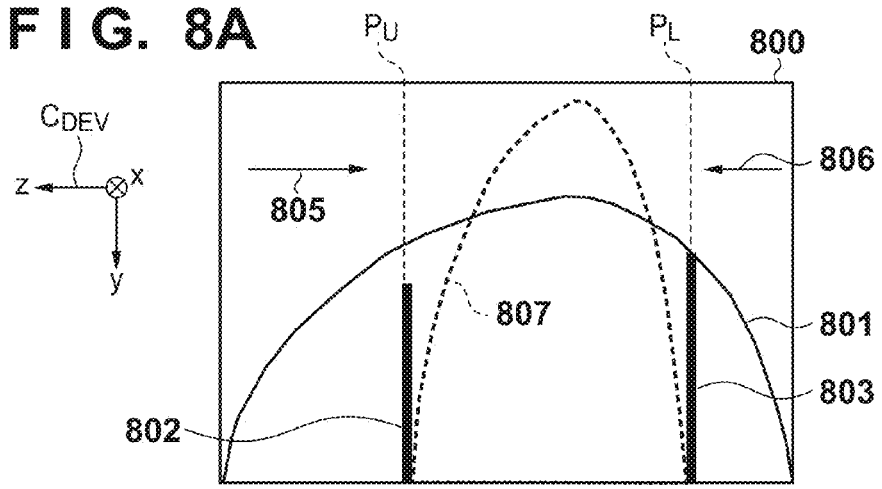
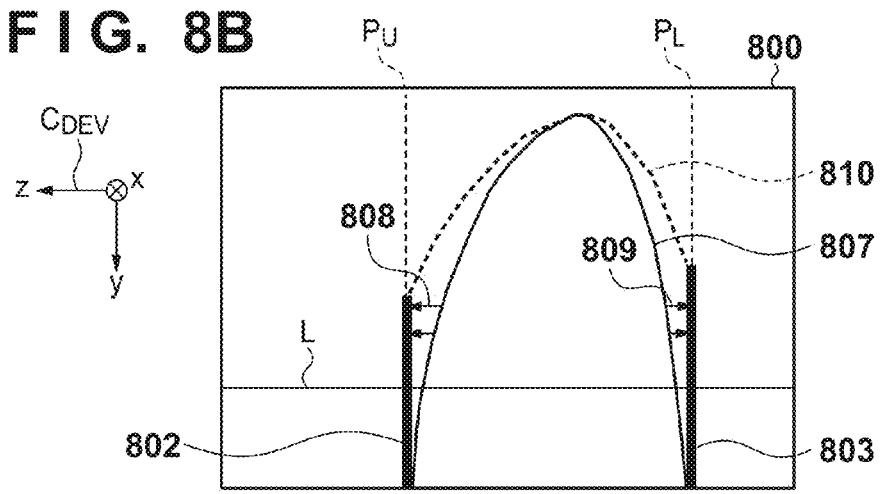
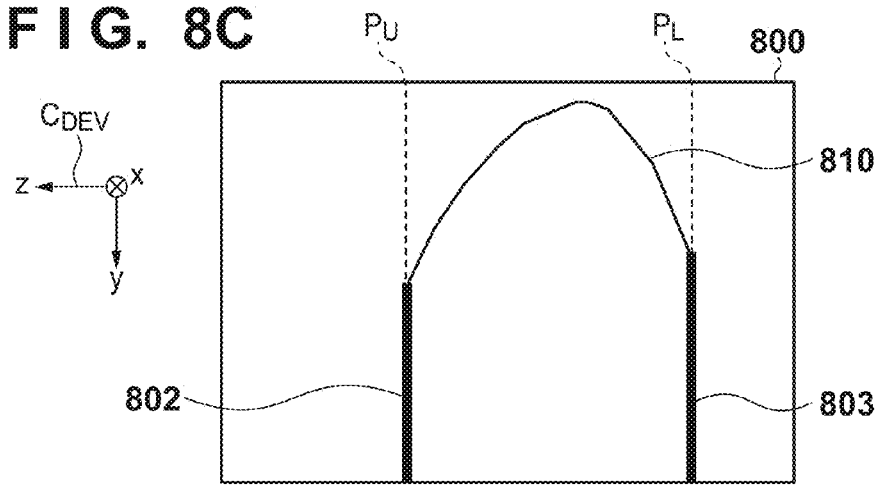

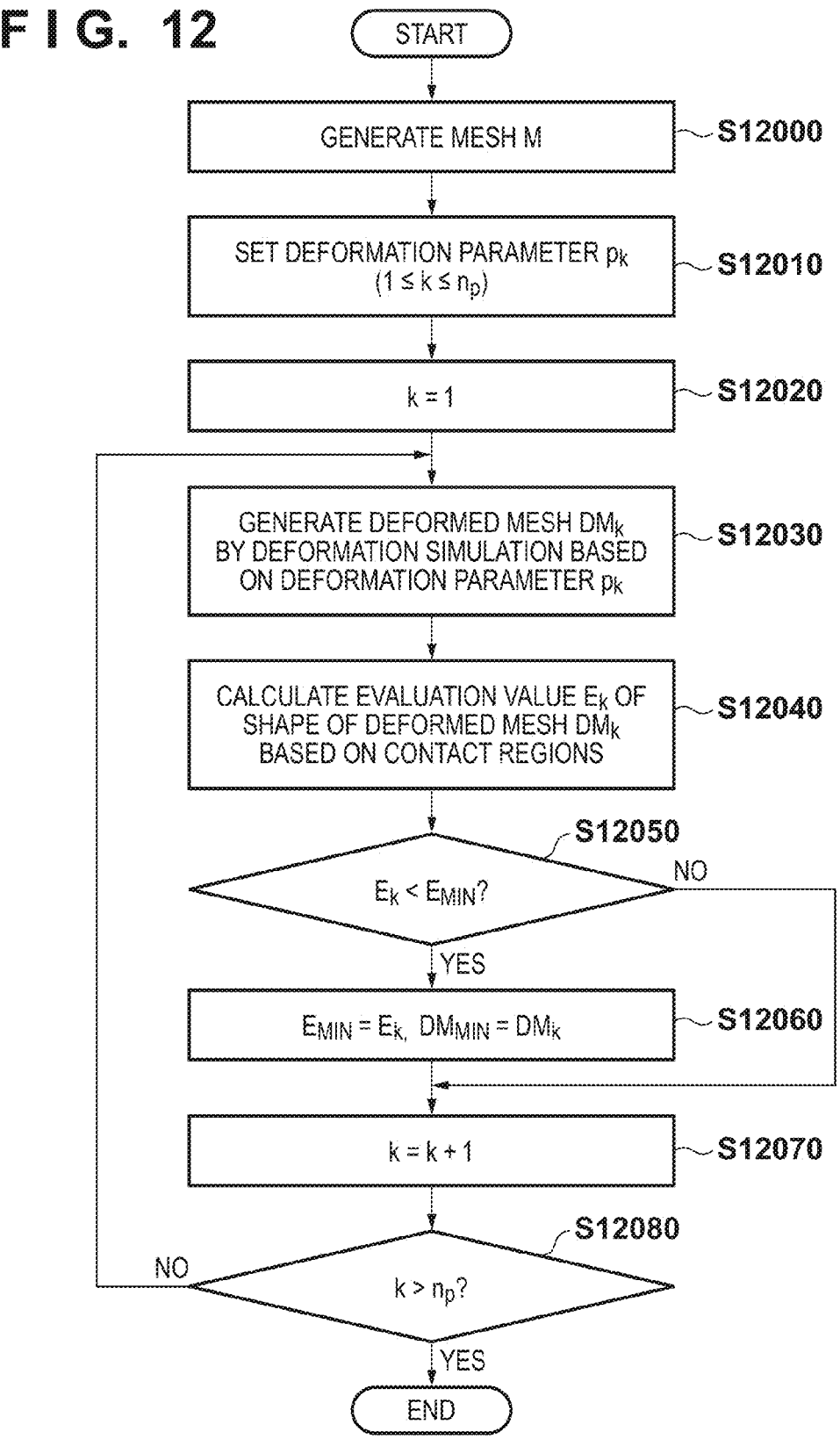

F I G. 15A
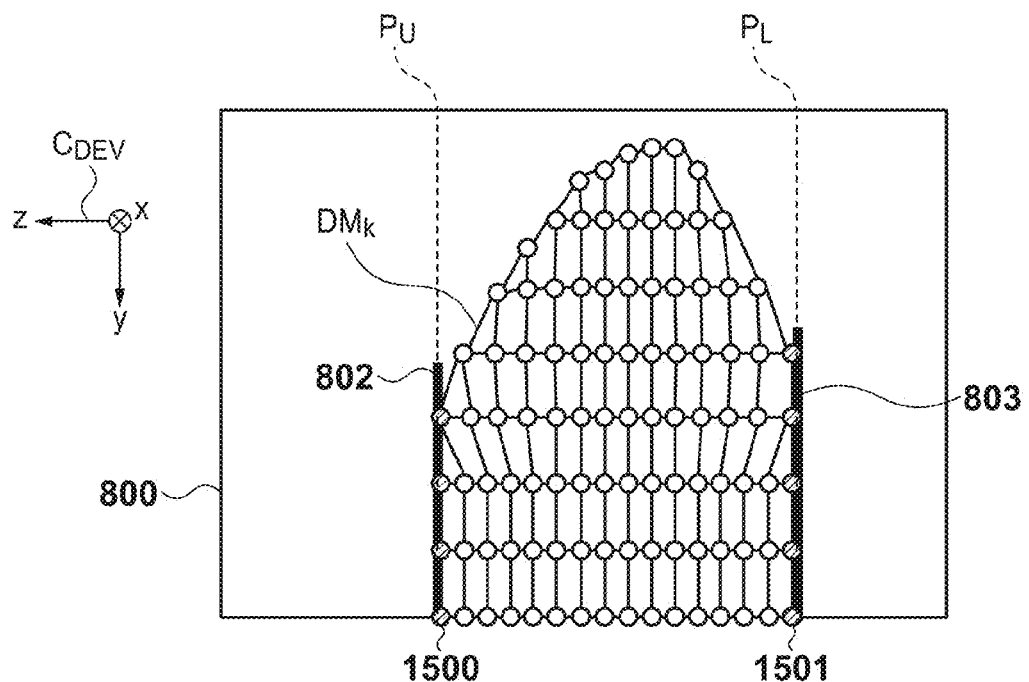
F I G. 15B
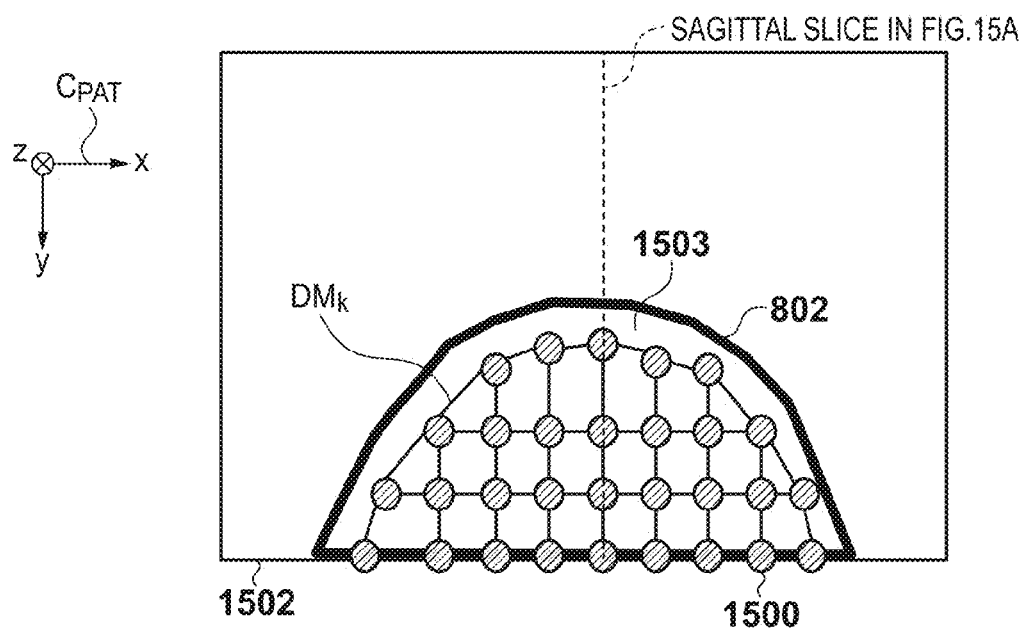

METHOD AND APPARATUS FOR ESTIMATING THE THREE-DIMENSIONAL SHAPE OF AN OBJECT

BACKGROUND OF THE INVENTION

1. Field of the Invention

The present invention relates to a technique of processing the medical images captured by various types of medical image acquisition apparatuses (modalities).

2. Description of the Related Art

Patent literature 1 (Japanese Patent Laid-Open. No. 2010-88627) discloses a PAT (Photoacoustic Tomography) apparatus. The PAT apparatus is an apparatus which excites an absorbing substance in a sample by irradiating a measurement target with optical pulses, and detects the photoacoustic signal generated by the thermoelastic expansion of the absorbing substance, thereby imaging properties associated with the light absorption of the measurement target. That is, the apparatus images an optical energy deposition amount distribution (optical energy absorption density distribution) in an object with respect to irradiation light. In addition, based on this distribution, the apparatus images the light absorption coefficient distribution of the object concerning an irradiation wavelength. In addition, it is possible to image the density distributions of substances constituting a living body based on light absorption coefficient distributions concerning a plurality of wavelengths. These images are expected to visualize information associated with a new blood vessel generated around a malignant tumor such as breast cancer. These images will be collectively referred to as photoacoustic tomographic images (PAT images) hereinafter.

PAT is designed to irradiate a human body with near-infrared pulses of low energy, and hence has difficulty in imaging a deep portion of the human body as compared with X-rays. Under the circumstance, according to patent literature 1, the PAT apparatus designed to measure breasts is used in a form such that a breast is held by two flat plates (to be referred to as holding plates hereinafter) and imaged while the thickness of the breast is reduced.

An image matching method is used as a method of aligning a PAT image with an MRI image. For example, non-patent literature 1 (Angela Lee, et al., "Breast X-ray and MR image fusion using finite element modeling", Proc. Workshop on Breast Image Analysis in conjunction with MICCAI 2011, pp. 129-136, 2011) discloses a technique for alignment between an X-ray mammography (MMG) image obtained by imaging a breast compressed by flat plates and an MRI image of the breast as in the case of PAT. Non-patent literature 2 (Iwashita, et al., "2D-3D Registration. Using 2D Distance Maps" in Meeting on Image Recognition and Understanding 2005 (MIRU 2005)) discloses a technique for high-speed alignment between a three-dimensional shape model of an object and a silhouette image of the object. In addition, patent literature 2 (Japanese Patent Laid-Open. No. 2008-235504) discloses a technique of detecting a part assembly error by comparing two-dimensional shape data recognized from a camera image of an assembly part with two-dimensional shape data obtained by projecting three-dimensional shape data of the assembly part in the viewpoint direction of the camera. Furthermore, non-patent literature 3 (C. Tanner, et al., "Breast Shapes on Real and Simulated Mammograms", Proc. Int. Workshop on Digital Mammography 2010 (IWDM 2010), LNCS 6136, pp. 540-547, 2010) discloses a technique of evaluating the shape of a breast after deformation which is obtained as a result of performing a physical deformation simulation by compression with flat plates with respect to an MRI image based on the two-dimensional shape of the breast which is extracted from an MMG image.

In addition, as described in patent literature 1, the PAT apparatus calculates an optical energy deposition amount distribution in an object from a detected photoacoustic signal. Since an optical energy deposition amount distribution is represented by the product of an absorption coefficient ($\mu a$) and a reaching light amount ($\Phi$), a light absorption coefficient distribution is calculated by dividing the optical energy deposition amount distribution by a light amount distribution. Since a light amount distribution is a three-dimensional distribution of light amounts in an inner region of an object, this calculation requires the three-dimensional shape of the object which is used to specify the inner region of the object. For example, according to patent literature 1, a simple three-dimensional shape of an object is acquired based on the two-dimensional measurement range set on the plane of each holding plate which holds a breast as an object and the region defined by the distance (the thickness of the object) between the two holding plates.

Since PAT and MRI images differ in their characteristics to be imaged, all the structures depicted in the MRI image do not match those on the PAT image. It is therefore difficult to execute high-accuracy alignment.

SUMMARY OF THE INVENTION

The present invention has been made in consideration of the above problem, and provides a technique for accurately estimating the three-dimensional shape of an object based on a deformed state of the object.

According to an aspect of the present invention, there is provided an image processing apparatus comprising: an acquisition unit configured to acquire a contact region between an object and a holding member based on an image obtained by imaging the object in a held state in which the object is held by the holding member; and an estimation unit configured to estimate a three-dimensional shape of the object in the held state based on the contact region.

According to another aspect of the present invention, there is provided an image processing method comprising: an acquisition step of acquiring a contact region between an object and a holding member based on an image obtained by imaging the object in a held state in which the object is held by the holding member; and an estimation step of estimating a three-dimensional shape of the object in the held state based on the contact region.

Further features of the present invention will become apparent from the following description of exemplary embodiments with reference to the attached drawings.

BRIEF DESCRIPTION OF THE DRAWINGS

FIG. 2 is a flowchart showing the processing performed by an image processing apparatus 100;

FIGS. 8A to 8C are views for explaining processing in step S2060;

FIG. 12 is a flowchart showing processing in step S11060;

FIGS. 15A and 15B are schematic views showing the positional relationship between a contact region and a deformed mesh;

DESCRIPTION OF THE EMBODIMENTS

The embodiments of the present invention will be described below with reference to the accompanying drawings. Note that each embodiment described below will exemplify a case in which the present invention is specifically carried out, and is a specific example of an arrangement described in the scope of claims.

First Embodiment

The following will exemplify an image processing apparatus which acquires a contact region between an object and holding members based on the images obtained by imaging the object in a held state in which the object is held by the holding members, and estimates the three-dimensional shape of the object in the held state based on the contact region.

More specifically, the image processing apparatus according to this embodiment implements high-accuracy alignment between a PAT image of a breast as an object of a subject and an MRI image of the breast, and improves the efficiency of diagnosis using both images. This apparatus extracts a region (contact region), of the breast, which is in contact with two transparent (capable of transmitting light) holding plates from an image obtained by imaging the outer appearance of the breast compressed by the holding plates. The apparatus then extracts the three-dimensional surface shape of the breast from an MRI image of the breast, and generates a deformed MRI image having undergone compression deformation alignment with respect to the MRI image using the extracted three-dimensional surface shape and the above contact region. Finally, the generated deformed MRI image and the PAT image are displayed side by side. The image processing apparatus according to this embodiment will be described below.

Figure 1:
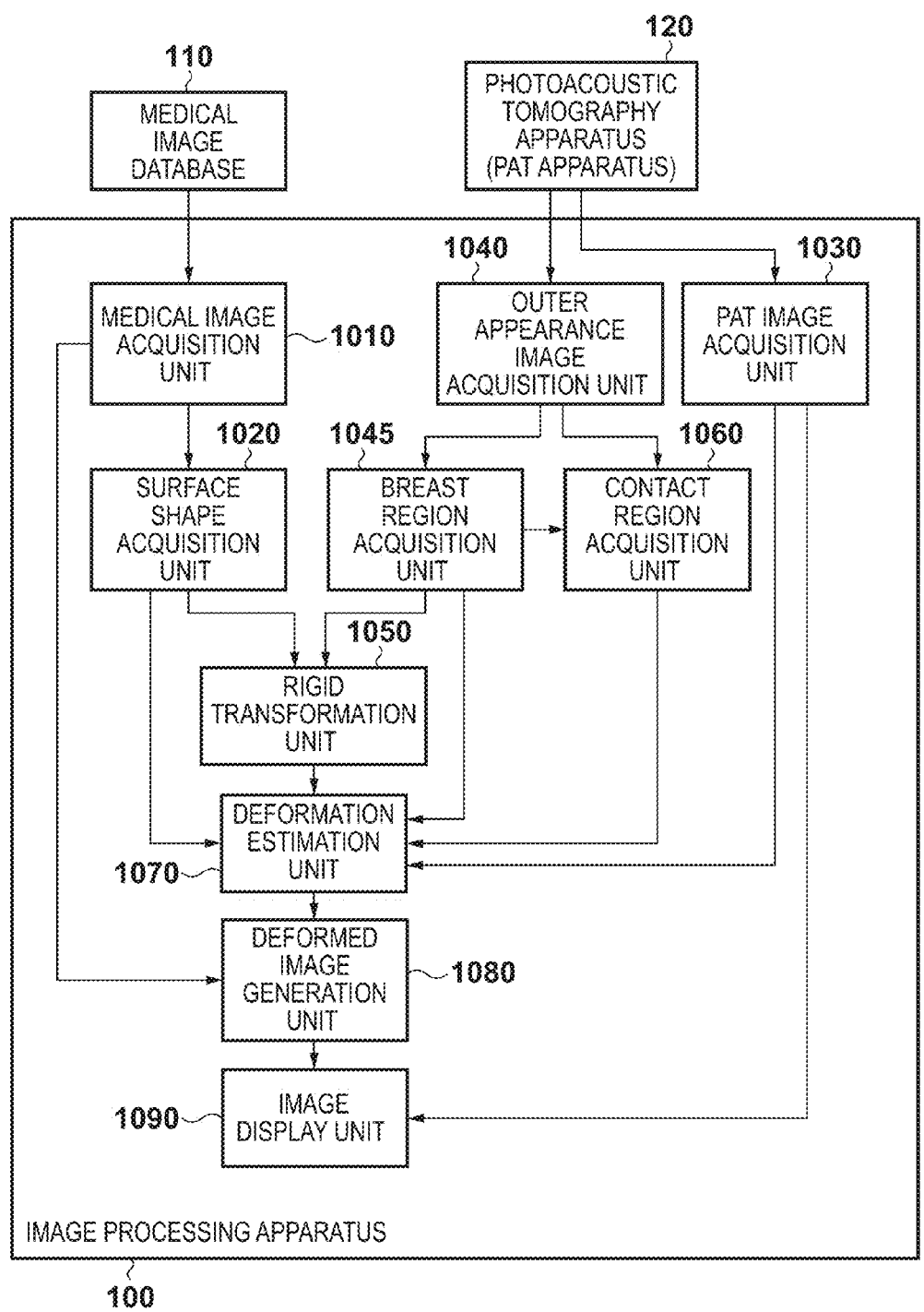
FIG. 1 is a block diagram showing an example of the functional arrangement of a system.

An example of the functional arrangement of a system according to this embodiment will be described first with reference to the block diagram of FIG. 1. As shown in FIG. 1, the system according to the embodiment includes an image processing apparatus 100, a medical image database 110, and a PAT (Photoacoustic Tomography) apparatus 120. The medical image database 110 and the PAT apparatus 120 are connected to the image processing apparatus 100.

Figure 3A:
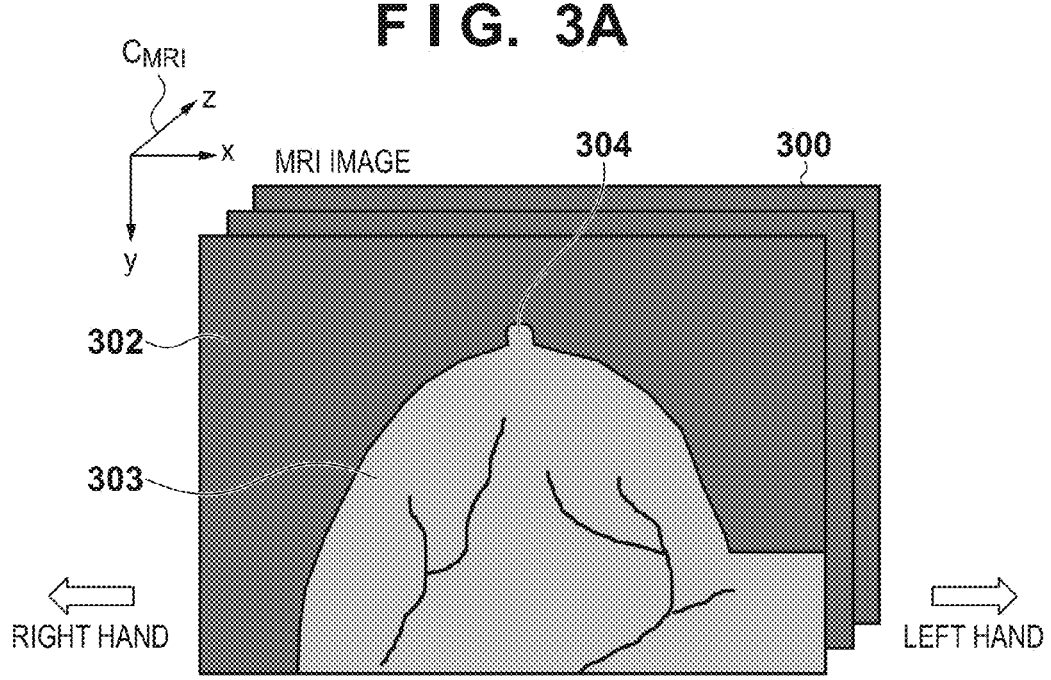
FIGS. 3A and 3B are views each showing an MRI image of a breast.
Figure 3B:
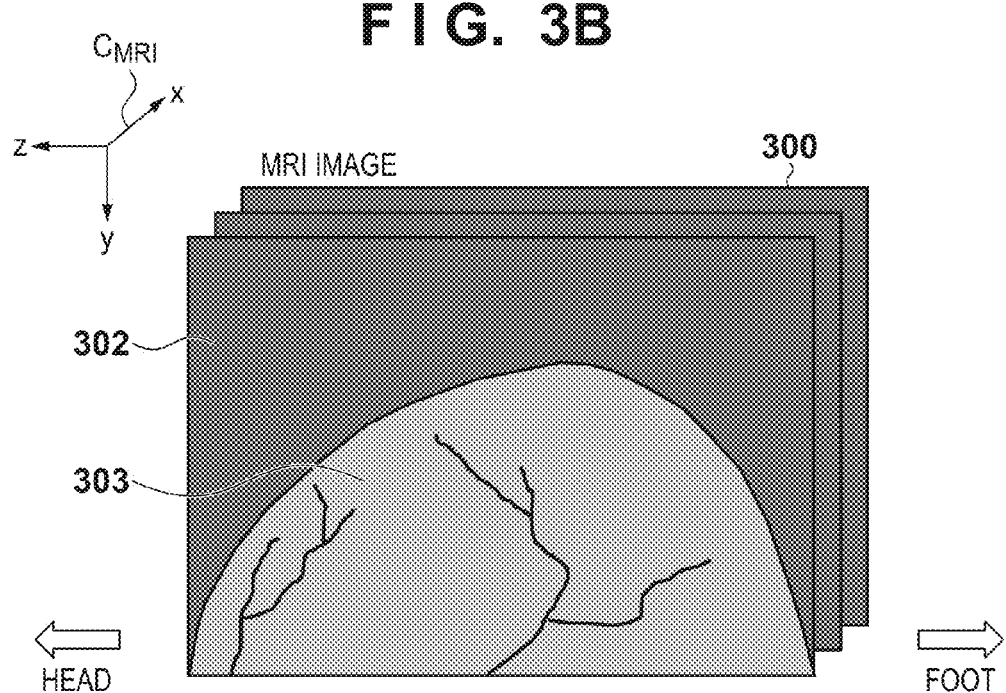

The medical image database 110 will be described first. The MRI images of a breast as an object are registered in the medical image database 110. The MRI images of the breast registered in the medical image database 110 will be described below. In the embodiment, each MRI image is three-dimensional image information. FIG. 3A is a schematic view showing a two-dimensional image (a slice containing a nipple 304) obtained by slicing the MRI image of the breast along a slice (axial slice) perpendicular to the craniocaudal direction of the human body. Assume that the three-dimensional coordinate position of a pixel in each two-dimensional image constituting an MRI image 300 in FIG. 3A is defined in an MRI image coordinate system $C_{MRI}$ as a coordinate system unique to the MRI image. Each two-dimensional image constituting the MRI image 300 includes a region 302 in which the outside of the body of a subject is depicted and a region 303 in which the inside of the body of the subject is depicted. FIG. 3B is a schematic view showing a two-dimensional image obtained by slicing the MRI image 300 along a slice (sagittal slice) perpendicular to the transverse direction of the human body. FIG. 3B shows the same image as in FIG. 3A. As shown FIGS. 3A and 3B, in this embodiment, the MRI image coordinate system $C_{MRI}$ is defined as a coordinate system in which the direction from the right-hand side to the left-hand side of the subject (patient) is the positive x-axis direction, the direction from the chest side to the back side of the patient is the positive y-axis direction, and the direction from the foot side to the head side is the positive z-axis direction.

The PAT apparatus 120 will be described next. The PAT apparatus 120 is an apparatus which captures PAT images. A PAT image of a breast as an object and an outer appearance image (camera image) as an image obtained by imaging the outer appearance of the breast are registered in the PAT apparatus 120. Note that the PAT image held by the PAT apparatus 120 of this embodiment includes an image obtained by imaging an optical energy deposition amount distribution in the object which corresponds to a plurality of wavelengths, an image obtained by imaging a light absorption coefficient distribution in the object which corresponds to the respective wavelengths, and an image obtained by imaging the degree of oxygen saturation of blood.

Figure 5:
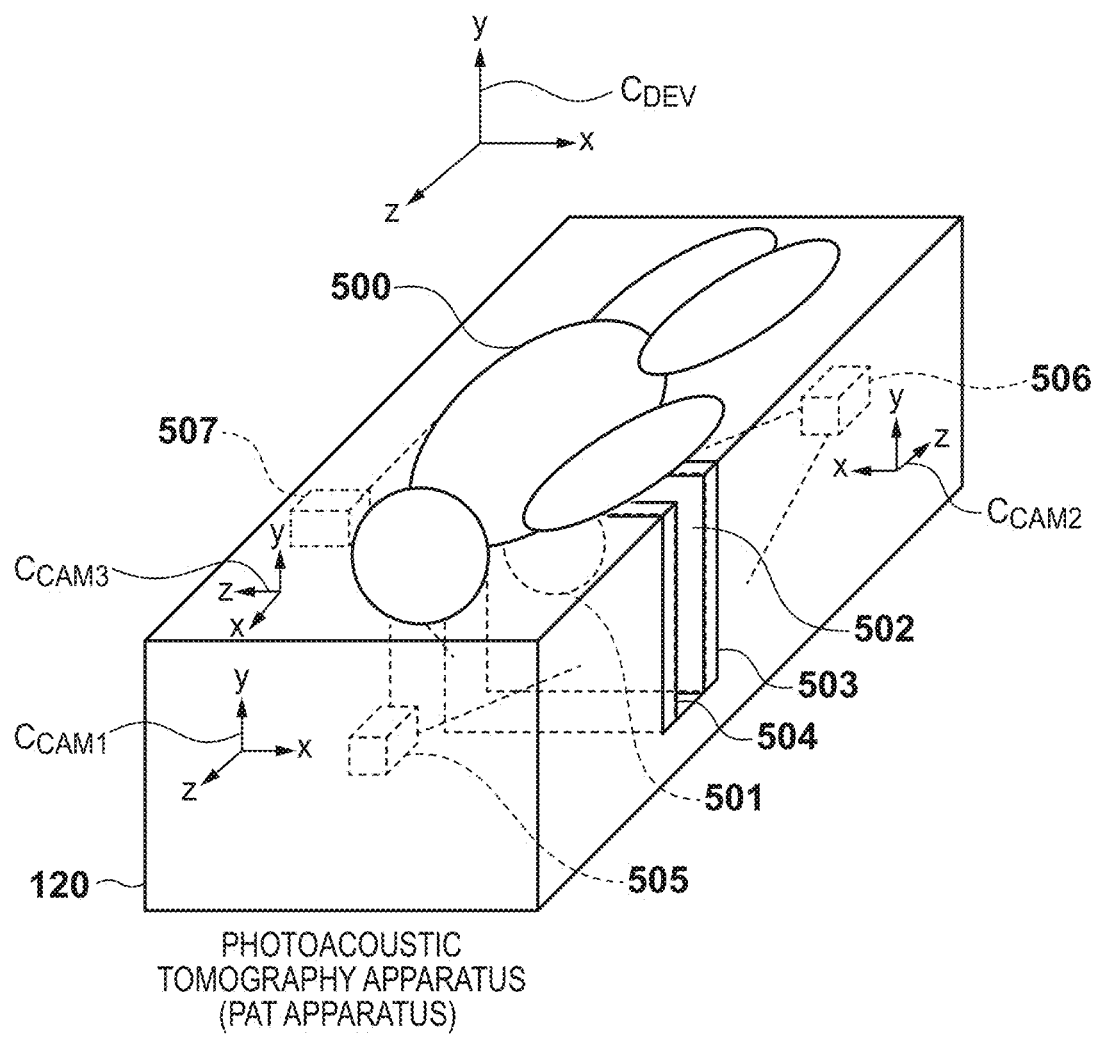
FIG. 5 is a view for explaining imaging of a breast by a PAT apparatus 120.

Breast imaging by the PAT apparatus 120 will be described below with reference to FIG. 5. Referring to FIG. 5, a subject 500 takes a prone position on a bed on the upper surface of the PAT apparatus 120. One breast 501 as an object is inserted into an opening portion 502 in the upper surface of the PAT apparatus 120. At this time, the breast 501 is held by two transparent holding plates (a holding plate 503 on the foot side and a holding plate 504 on the head side) in a compressed state so as to allow irradiation light to reach the inside of the breast 501, and is imaged while its thickness is reduced. The breast 501 is held by the holding plate 503 and the holding plate 504 by moving the holding plate 504 as a movable plate on the head side toward the foot side relative to the fixed holding plate 503 on the foot side. Assume that in this embodiment, both the holding plate 503 and the holding plate 504 are flat plates, and surfaces (to be referred to as holding surfaces hereinafter) which come into contact with the breast are planes. Assume also that the PAT apparatus 120 has already measured the holding thickness at the time of holding (the distance between the holding plate 503 and the holding plate 504), and the measured thickness is held in the header portion of a PAT image as additional information of the image. A light source (not shown) applies near-infrared pulses as irradiation light from a direction perpendicular to the planes of the holding plates 503 and 504. An ultrasonic probe (not shown) arranged perpendicularly to the planes of the holding plates 503 and 504 receives a photoacoustic signal generated in the body.

A PAT apparatus coordinate system $C_{DEV}$ is defined for the PAT apparatus 120, which is a coordinate system unique to the apparatus. The x-y plane is parallel to the holding plates 503 and 504, and the z-axis extends in a direction perpendicular to the holding plates 503 and 504 (the thickness direction of the held breast). In the PAT apparatus coordinate system $C_{DEV}$, for example, as in the MRI image coordinate system $C_{MRI}$, the direction from the right-hand side to the left-hand side of the patient is defined as the positive x-axis direction, the direction from the chest side (lower side) to the back side (upper side) is defined as the positive y-axis direction, and the direction from the foot side to the head side is defined as the positive z-axis direction. The origin of the PAT apparatus coordinate system $C_{DEV}$ is set at, for example, the lower end position on the right-hand side on the holding plate 503. Assume that the PAT apparatus 120 will subsequently handle the relationships between this coordinate system as a reference and other coordinate systems.

Figure 6:
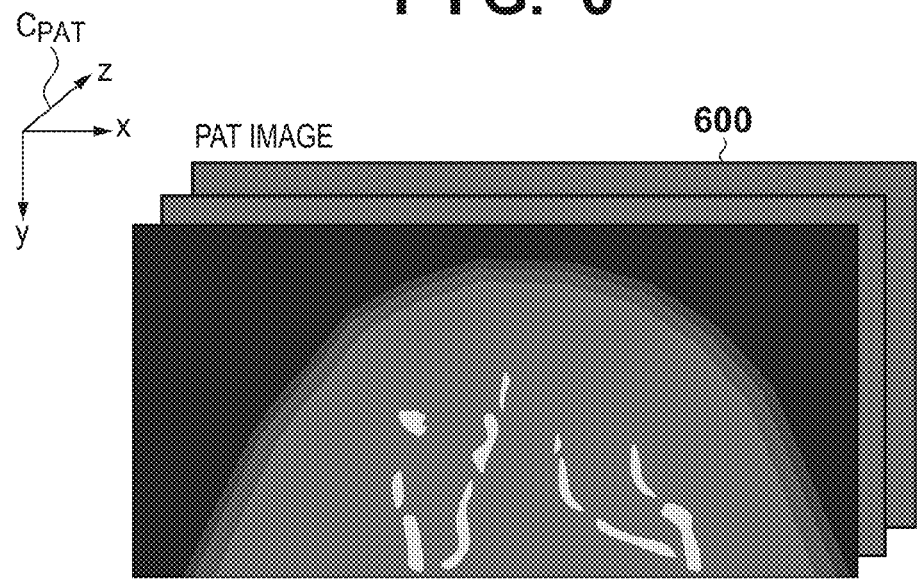
FIG. 6 is a view showing an example of a PAT image.

FIG. 6 is a view showing an example of the PAT image captured by the PAT apparatus 120. In this embodiment, a PAT image 600 is three-dimensional image information. Like FIG. 3A, FIG. 6 is a schematic view of an axial slice. As shown in FIG. 6, in the embodiment, like the MRI image coordinate system $C_{MRI}$, a PAT image coordinate system $C_{PAT}$ is defined as a coordinate system in which the direction from the right-hand side to the left-hand side of the patient is the positive x-axis direction, the direction from the chest side to the back side is the positive y-axis direction, and the direction from the foot side to the head side is the positive z-axis direction. At this time, a coordinate transformation matrix which performs transformation from the PAT image coordinate system $C_{PAT}$ to the PAT apparatus coordinate system $C_{DEV}$ is defined as $T_{PtoD}$. Assume that all the coordinate transformation matrices appearing in the following description are 4×4 matrices each representing the translation and rotation of the coordinate system. The rotation component of the PAT image coordinate system $C_{PAT}$ matches that of the PAT apparatus coordinate system $C_{DEV}$, and the origin position of $C_{PAT}$ changes in accordance with the imaging range of an object. That is, the coordinate transformation matrix $T_{PtoD}$ can be uniquely calculated based on an imaging range. Assume that the coordinate transformation matrix $T_{PtoD}$ is stored as additional information of the PAT image in the header portion of the image.

In addition, as shown in FIG. 5, the PAT apparatus 120 is equipped with three cameras (a front camera 505, a rear camera 506, and a side camera 507) for imaging the state of an object (the outer appearance of the breast). The front camera 505 is installed at a position where it can image the outer appearance of the breast from the head side through the holding plate 504. The rear camera 506 is installed at a position where it can image the outer appearance of the breast from the leg side through the holding plate 503. The side camera 507 is installed at a position where it can image the outer appearance of the breast from a side surface. The PAT apparatus 120 stores images of the breast in an unheld state (a state in which the breast is not compressed and held by the holding plates 503 and 504) and in a held state (a state in which the breast is compressed and held by the holding plates 503 and 504) which are imaged by these cameras. In the following description, images captured by the front camera 505, the rear camera 506, and the side camera 507 in a held state are respectively represented by $I_{CAM1}$, $I_{CAM2}$, and $I_{CAM3}$. In addition, images captured by the front camera 505, the rear camera 506, and the side camera 507 in an unheld state are respectively represented by $I'_{CAM1}$, $I'_{CAM2}$, and $I'_{CAM3}$. $C_{CAM1}$ represents a coordinate system (front camera coordinate system) of the front camera 505, in which the z-axis (the negative direction of a visual axis) faces in almost the same direction as that of the z-axis of the PAT apparatus coordinate system $C_{DEV}$. Likewise, $C_{CAM2}$ represents a coordinate system (rear camera coordinate system) of the rear camera 506, in which the z-axis faces in almost the opposite direction to the z-axis of the PAT apparatus coordinate system $C_{DEV}$. $C_{CAM3}$ represents a coordinate system (side camera coordinate system) of the side camera 507, in which the z-axis faces in the opposite direction to the x-axis direction of the PAT apparatus coordinate system $C_{DEV}$. In this case, coordinate transformation matrices for transformation from $C_{CAM1}$, $C_{CAM2}$, and $C_{CAM3}$ to the PAT apparatus coordinate system $C_{DEV}$ are respectively defined as $T_{C1toD}$, $T_{C2toD}$, and $T_{C3toD}$. Assume that these cameras have been calibrated in the PAT apparatus coordinate system $C_{DEV}$, and the image processing apparatus 100 holds the above coordinate transformation matrices and internal parameters as known information. Note that $T_{C1toD}$, $T_{C2toD}$, and $T_{C3toD}$ may be held as additional information of the PAT image in the header portion of the image.

Figure 7:
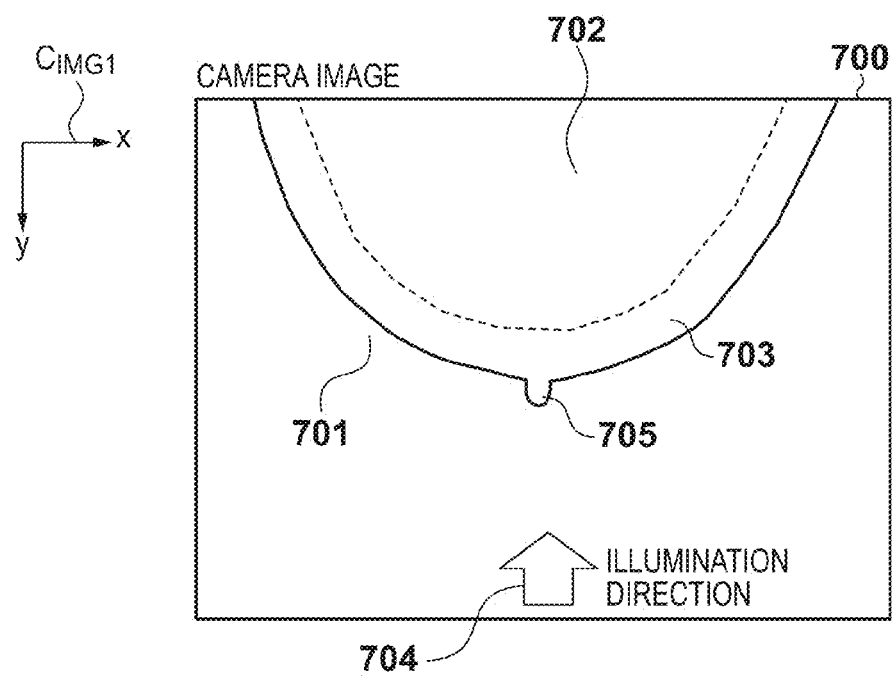
FIG. 7 is a view showing an example of the image captured by a front camera 505.

FIG. 7 shows an example of an image 700 ($I_{CAM1}$) captured by the front camera 505 in a held state. A breast region 701 in the image 700 is a region where the breast in a held state is depicted. The breast region 701 is constituted by a region (contact region) 702 of the breast which is in contact with the holding plate (holding plate 504) and a region (noncontact region) 703 which is not in contact with the holding plate (holding plate 504). In this case, the noncontact region 703 of the breast in a held state, which light directly strikes, can be depicted brightly, and the contact region 702, which light does not directly strike, can be depicted darkly by installing an illumination device (not shown) on the bottom surface of the PAT apparatus and applying illumination in the y-axis direction (an illumination direction 704 in FIG. 7) of the PAT apparatus coordinate system $C_{DEV}$.

Note that coordinates on a front camera image coordinate system $C_{IMG1}$ (two-dimensional) as a coordinate system unique to the image $I_{CAM1}$ captured by the front camera 505 are represented on the camera coordinate system $C_{CAM1}$ (three-dimensional) in the following manner. That is, such coordinates are expressed as a line segment passing through the focal position of the front camera 505 and each position on a projection plane of the front camera 505. Since a coordinate transformation method used between a general camera image and a three-dimensional space is used for transformation between a camera image coordinate system and a camera coordinate system, a description of the method will be omitted. The same applies to the rear camera 506 and the side camera 507, and hence a description about them will be omitted.

Although in this embodiment, the breast of the human body is used as an object, the present invention is not limited to this, and any region of the human body which can be held by the holding plates can be used. In addition, although in the embodiment, MRI images are used as images registered in the medical image database 110, any three-dimensional medical images obtained by imaging the living body can be used. Furthermore, the PAT apparatus 120 is used as an apparatus which images an object in a held state, any image sensing device including holding plates can be used.

The processing performed by the image processing apparatus 100 will be described next with reference to FIG. 2 showing a flowchart for the processing.

(Step S2000: Acquisition of MRI Image)

In step S2000, a medical image acquisition unit 1010 acquires the MRI image 300 of the breast registered in the medical image database 110, and sends the acquired MRI image 300 to a surface shape acquisition unit 1020 and a deformed image generation unit 1080 which are provided on the subsequent stage.

(Step S2010: Acquisition of Surface Shape and Nipple Position from MRI Image)

In step S2010, the surface shape acquisition unit 1020 detects pixels constituting the surface of the breast from each two-dimensional image constituting the MRI image 300, and acquires a set of three-dimensional coordinate positions (surface positions) defined concerning the detected pixels as the surface shape (shape information) of the breast. In addition, the surface shape acquisition unit 1020 acquires a nipple position in the MRI image 300 based on the three-dimensional curvature of the acquired surface shape. The surface shape acquisition unit 1020 then sends the acquired surface shape and nipple position to a rigid transformation unit 1050 and a deformation estimation unit 1070 which are provided on the subsequent stage.

Figure 4A:
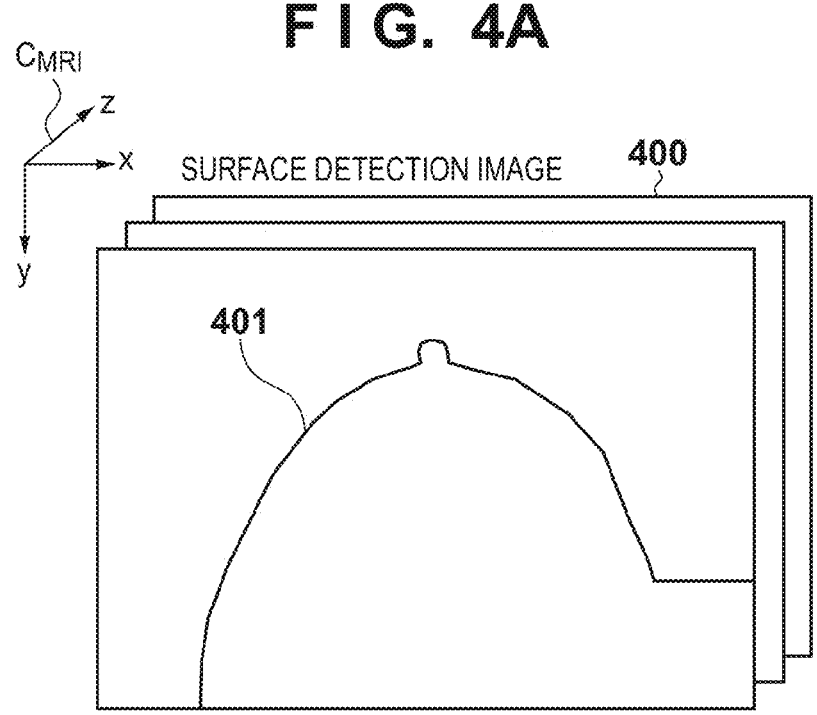
FIGS. 4A and 4B are views for explaining the processing performed by a surface shape acquisition unit 1020.
Figure 4B:
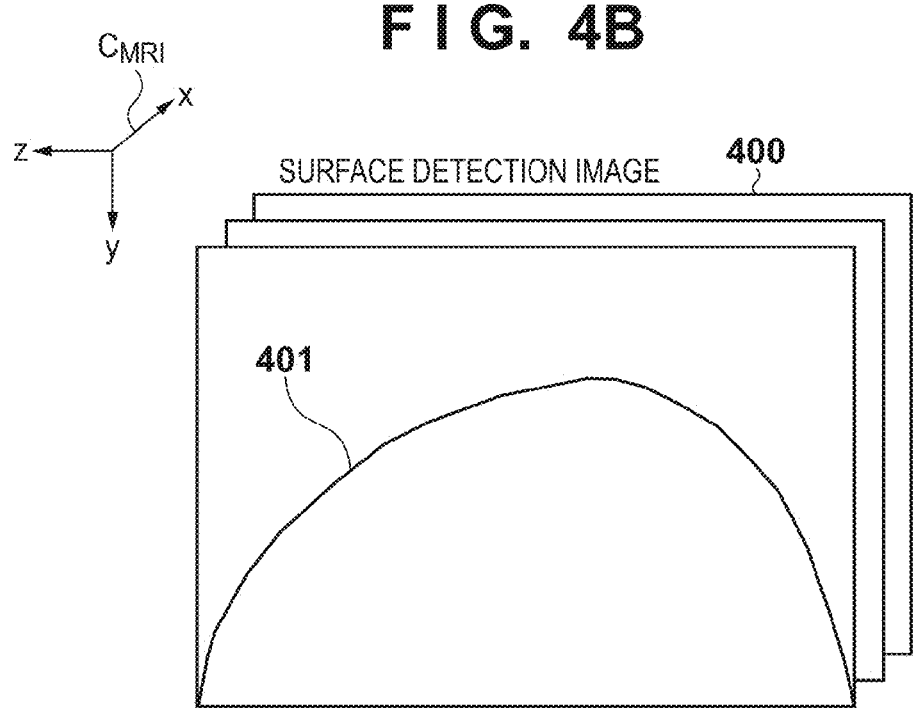

The processing performed by the surface shape acquisition unit 1020 to acquire the surface shape of the breast from the MRI image 300 will be described below with reference to FIGS. 4A and 4B. Referring to FIG. 4A, an image 400 (surface detection image) is obtained by detecting a surface position 401 serving as the boundary between the region 302 outside the body of the object and the region 303 inside the body in each two-dimensional image constituting the MRI image 300 in FIG. 3A. The surface detection image 400 may be an image in which the boundary line between the region outside the body of the object and the region inside the body in each two-dimensional image constituting the MRI image explicitly appears. A surface detection image is, for example, a binary image with each pixel constituting a boundary line (a surface of an object) having a pixel value of 1, and each pixel constituting a portion other than the boundary line having a pixel value of 0.

The surface shape acquisition unit 1020 performs image processing for the MRI image 300 to detect the surface position 401, thereby generating the surface detection image 400 described above. Various methods are conceivable as methods of detecting the surface position 401. For example, such a method can be implemented by obtaining the spatial gradient of the luminance values of the MRI image 300 and performing threshold processing for the magnitude of the spatial luminance gradient. A method of detecting the surface position 401 of the object is not limited to this, and any known existing method may be used.

The surface shape acquisition unit 1020 further acquires a pixel used as a surface point from the pixels constituting the surface position 401 by processing the surface detection image 400. For example, the surface shape acquisition unit 1020 may acquire pixels from the pixels constituting the surface position 401 at predetermined intervals or all the pixels constituting the surface position 401 as surface points. A set of three-dimensional coordinate positions defined concerning the surface points represents the surface shape of the breast.

The image processing apparatus 100 need not always acquire surface positions by processing the MRI image 300. For example, each two-dimensional image constituting the MRI image 300 may be displayed on a suitable monitor to allow the user to acquire, as the surface position 401, the boundary line designated on the displayed two-dimensional image with a mouse, keyboard, or the like (not shown).

In the following description, $N_S$ pixels of all the pixels constituting the surface position 401 in all the two-dimensional images constituting the MRI image 300 are set as surface points $P_{Si}$ ($1 \leq i \leq N_S$) instead of all the pixels. The positions of the surface points $P_{Si}$ are recorded in a memory (not shown) in the image processing apparatus 100 as three-dimensional position coordinate vectors $v_{Si\_MRI}$ ($1 \leq i \leq N_S$) in the MRI image coordinate system $C_{MRI}$. In this embodiment, the surface shape of the breast acquired from the MRI image is a shape model of the breast in an upheld state (a three-dimensional shape model of the object before contacting the holding members).

(Step S2020: Acquisition of PAT Image)

In step S2020, a PAT image acquisition unit 1030 acquires, from the PAT apparatus 120, a PAT image of the breast imaged by the PAT apparatus 120. The PAT image acquisition unit 1030 may directly acquire a PAT image in synchronism with imaging by the PAT apparatus 120 or may acquire a PAT image from a medical image recording apparatus (not shown) in which the images captured in the past by the PAT apparatus 120 are recorded. The PAT image acquisition unit 1030 then sends the acquired PAT image to an image display unit 1090 on the subsequent stage. The PAT image acquisition unit 1030 also sends information required in the following processing such as the additional information contained in the header of the PAT image and various types of information held by the image processing apparatus 100, for example, $T_{PtoD}$, $T_{C1toD}$, $T_{C2toD}$, and $T_{C3toD}$, to the deformation estimation unit 1070. Assume that in this embodiment, the PAT image acquired by the PAT image acquisition unit 1030 is a three-dimensional image obtained by imaging an optical energy deposition amount distribution in the breast with respect to predetermined wavelengths.

(Step S2030: Acquisition of Camera Image)

In step S2030, an outer appearance image acquisition unit 1040 acquires, from the PAT apparatus 120, outer appearance images of the breast in an upheld state and a held state which are captured by the front camera 505, the rear camera 506, and the side camera 507. That is, the outer appearance image acquisition unit 1040 acquires $I_{CAM1}$, $I_{CAM2}$, $I_{CAM3}$, $I'_{CAM1}$, $I'_{CAM2}$, and $I'_{CAM3}$ from the PAT apparatus 120. The outer appearance image acquisition unit 1040 then sends these acquired outer appearance images to a breast region acquisition unit 1045 and a contact region acquisition unit 1060 which are provided on the subsequent stage.

(Step S2035: Acquisition of Breast Region and Nipple Position from Camera Image)

In step S2035, the breast region acquisition unit 1045 performs image processing for each outer appearance image received from the outer appearance image acquisition unit 1040 to acquire a breast region on the outer appearance image (701 in FIG. 7). The breast region acquisition unit 1045 also acquires the position of the nipple (705 in FIG. 7) on the outer appearance image.

It is possible to detect the breast region 701 by using, for example, an HSV color space as a general technique for skin color detection. More specifically, it is possible to detect a breast region by converting the color space of the outer appearance image into an HSV color space and detecting pixels whose hues H (Hue) fall within a predetermined range. In addition, it is possible to detect, as the position of the nipple, a position, on a curve representing the boundary of the breast region, which exhibits the largest curvature. Note that the method of detecting a breast region and a nipple position is not limited to this method.

The breast region acquisition unit 1045 then sends the breast region and the position of the nipple acquired by the above processing to the rigid transformation unit 1050, the contact region acquisition unit 1060, and the deformation estimation unit 1070 which are provided on the subsequent stage.

(Step S2040: Rigid Alignment between MRI Image Coordinate System and PAT Image Coordinate System)

In step S2040, the rigid transformation unit 1050 performs rigid alignment between the MRI image coordinate system $C_{MRI}$ and the PAT apparatus coordinate system $C_{DEV}$. That is, the rigid transformation unit 1050 derives a coordinate transformation matrix $T_{MtoD}$ for transformation from the MRI image coordinate system $C_{MRI}$ to the PAT apparatus coordinate system $C_{DEV}$. This processing is performed based on the nipple position in the MRI image which is acquired in step S2010 and the nipple position on the outer appearance image in an unheld state which is acquired in step S2035. Assume that in this embodiment, the posture of the breast in the PAT apparatus coordinate system $C_{DEV}$ almost matches that in the MRI image coordinate system $C_{MRI}$, and coordinate transformation from the MRI image coordinate system $C_{MRI}$ to the PAT apparatus coordinate system $C_{DEV}$ can be written by only translation.

First of all, the rigid transformation unit 1050 calculates a three-dimensional nipple position in an unheld state from the two-dimensional nipple position in an unheld state which is obtained from each outer appearance image, based on the triangulation principle. For example, it is possible to obtain a three-dimensional nipple position from two-dimensional nipple positions on the respective outer appearance images captured by the front camera and the side camera whose directions differ by 90° from each other. Likewise, it is also possible to calculate a three-dimensional nipple position from two-dimensional nipple positions on the respective outer appearance images captured by the rear camera and the side camera. The translation component of $T_{MtoD}$ is then calculated such that the nipple position in the MRI image matches the three-dimensional nipple position in an upheld state which is obtained from the outer appearance image.

(Step S2050: Acquisition of Contact Region from Outer Appearance Image)

In step S2050, the contact region acquisition unit 1060 performs image processing for the breast regions in the outer appearance images ($I_{CAM1}$ and $I_{CAM2}$) in a held state to detect the contact regions 702 on the outer appearance images. The contact region acquisition unit 1060 calculates the three-dimensional position (region information) of the contact region in the PAT apparatus coordinate system $C_{DEV}$ based on the information of each detected contact region and the position information of the holding plates 503 and 504. The contact region acquisition unit 1060 then sends the calculated three-dimensional position of the contact region to the deformation estimation unit 1070 on the subsequent stage.

In this embodiment, the processing of discriminating the contact region 702 and the noncontact region 703 is performed from the breast region 701 acquired in step S2035. As described above, it is possible to depict the contact region 702 and the noncontact region 703 in FIG. 7 on the outer appearance image with different brightnesses by causing the illumination device installed on the bottom surface of the PAT apparatus to apply illumination to the breast in a held state. It is therefore possible to detect the contact region 702 by, for example, detecting each pixel whose brightness (Value) in the HSV color space is lower than a threshold from the respective pixels of the breast region 701. However, the method of detecting the contact region 702 is not limited to this method. For example, it is possible to detect pixels each of whose average RGB value in the RGB color space is smaller than a threshold. Assume that in the following description, $N_{C1}$ pixels are acquired as pixels constituting a contact area on the outer appearance image $I_{CAM1}$ captured by the front camera, and $N_{C2}$ pixels are acquired as pixels constituting a contact area on the outer appearance image $I_{CAM2}$ captured by the rear camera.

Note that a contact area need not always be acquired by image processing for an outer appearance image. For example, an outer appearance image may be displayed on a monitor, and the user may designate a contact area on an outer appearance image by operating the mouse, keyboard, or the like (not shown).

The three-dimensional position of the contact region in the PAT apparatus coordinate system $C_{DEV}$ is then calculated. In this case, the contact region depicted in the outer appearance image $I_{CAM1}$ captured by the front camera 505 exists on the holding surface of the holding plate 504. It is therefore possible to obtain a three-dimensional position (three-dimensional position information) $v_{Uj\_DEV}$ ($1 \leq j \leq N_{C1}$) of a point on the holding plate 504 which corresponds to each pixel constituting the contact region in the outer appearance image $I_{CAM1}$ in the following manner. That is, it is possible to obtain a three-dimensional position as an intersection point between a plane $P_U$ representing the holding surface of the holding plate 504 and a straight line (visual line) connecting the projection center position of the front camera and each pixel position (two-dimensional position information) constituting the contact region in the outer appearance image $I_{CAM1}$. This computation can be implemented by obtaining an equation for each visual line in the front camera coordinate system based on the internal parameters of the front camera and obtaining an intersection point with the plane $P_U$ upon transforming the obtained equation into the PAT apparatus coordinate system $C_{DEV}$ using the coordinate transformation matrix $T_{C1toD}$.

Likewise, it is possible to obtain, as a point on a plane $P_L$ representing the holding surface of the holding plate 503, a three-dimensional position $v_{Lj\_DEV}$ ($1 \leq j \leq N_{C2}$) of a point on the holding plate 503 which corresponds to each pixel constituting the contact region in the camera image $I_{CAM2}$ captured by the rear camera. Assume that as described above, the holding plate 503 is fixed to the apparatus coordinate system, and that in this embodiment, the image processing apparatus 100 holds the position of the plane $P_L$ as known information. In addition, in the embodiment, the position of the plane $P_U$ has been calculated based on holding thickness information held as additional information by a PAT image. For example, information indicating that the plane $P_L$ is positioned on z=0 plane is stored. If the holding thickness is 50 mm, the plan $P_U$ is calculated to be positioned on z=50 plane.

(Step S2060: Deformation Estimation Using Contact Region)

In step S2060, by using the contact region information acquired in step S2050 as constraints, the deformation estimation unit 1070 estimates the surface shape (estimate value) of the breast after compression deformation from the surface shape of the breast obtained from the MRI image. In this embodiment, this estimation is performed by obtaining a deformation function $F_{DEV}(x, y, z)$ such that the calculated contact region obtained when deformation processing is performed for the breast in the MRI image by using the deformation function $F_{DEV}(x, y, z)$ matches (almost matches) the contact region acquired in step S2050. Note that "almost matches" in this embodiment includes "perfectly matches".

More specifically, first of all, coordinate transformation using a coordinate transformation matrix $T_{MtoD}$ obtained in step S2040 is applied to the three-dimensional coordinate position $v_{Si\_MRI}$ of each surface point as the surface shape of the breast acquired in step S2010. As a result of this coordinate transformation, the three-dimensional coordinate position $v_{Si\_MRI}$ of each surface point in the MRI image coordinate system $C_{MRI}$ is transformed into a three-dimensional coordinate position (position coordinate vector) $v_{Si\_DEV}$ ($1 \leq i \leq N_S$) in the PAT apparatus coordinate system $C_{DEV}$.

The deformation estimation unit 1070 then obtains the deformation function $F_{DEV}(x, y, z)$ such that the position corresponding to the contact region obtained as a result of deforming $v_{Si\_DEV}$ (that is, the three-dimensional position information of the calculated contact region) matches (coincides with) the three-dimensional position information of the contact region acquired in step S2050. The processing performed in this step will be described below with reference to FIGS. 8A to 8C.

FIGS. 8A to 8C are schematic views showing how deformation estimation is performed by compression deformation using a contact region. In addition, FIGS. 8A to 8C are schematic views each showing a two-dimensional plane when a processing target region of a breast is sliced along a sagittal slice. This plane represents a plane perpendicular to each of the holding plates 503 and 504 in the PAT apparatus coordinate system $C_{DEV}$.

FIG. 8A is a view showing processing for compression deformation of a target region in the z-axis direction by affine transformation as the first step in deformation estimation. FIG. 8A shows a processing target region 800, a surface position 801 of the breast (that is, $v_{Si\_DEV}$), a contact region 802 with the holding plate 504 (that is, $v_{Uj\_DEV}$), a contact region 803 (that is, $v_{Lj\_DEV}$) with the holding plate 503, compression directions 805 and 806, and a surface position 807 of the breast after compression deformation. In the first step, the breast is roughly divided into the upper half portion (head side) and the lower half portion (foot side), and affine transformation is applied to each portion based on information such as a holding thickness.

In compression deformation using the two holding plates, deformation occurs toward the center of the region sandwiched between the two holding plates as indicated by the compression directions 805 and 806. In this embodiment, therefore, the target region is divided into two regions defined by $z > z_M$ and $z \leq z_M$, and different deformations are applied to the respective regions. That is, affine transformation is applied to the former region so as to perform scaling in the direction in which compression occurs such that the z position shifts from $z_{MAX}$ to $z_U$. Likewise, affine transformation is applied to the latter region so as to perform scaling in the direction in which compression occurs such that the z position shifts from $z_{MIN}$ to $z_L$. To perform this processing, a scale factor $s_{Z1}$ in the z-axis direction is calculated by $$s_{Z1} = (z_U - z_M)/(z_{MAX} - z_M) \text{ (if } z > z_M) \quad (1)$$

$$s_{Z1} = (z_L - z_M)/(z_{MIN} - z_M) \text{ (if } z \leq z_M) \quad (2)$$

where $z_U$ represents the z-coordinate of the plane $P_U$, $z_L$ represents the z-coordinate of the plane $P_L$, $z_M$ represents the z-coordinate of the middle point between $z_U$ and $z_L$, and $z_{MAX}$ and $z_{MIN}$ respectively represent the maximum and minimum values of the z position in a position coordinate vector $v_{Si\_DEV}$ of the surface position 801.

A scale factor $s_{Y1}$ in the y-axis direction is calculated next. First of all, the three-dimensional position of the nipple in a held state is obtained based on the triangulation principle by using a nipple position on each outer appearance image in a held state. In this case, the three-dimensional position of the nipple in an unheld state has been calculated by the processing in step S2040. The ratio of elongation of the breast in the y-axis direction is obtained by using the change ratio of the y-coordinate of the three-dimensional position of the nipple accompanying deformation from an unheld state to a held state. The obtained ratio is represented by $s_{Y1}$. Finally, a scale factor $s_{X1}$ in the x-axis direction is calculated. In this case, assume that the volume of the object is stored before and after holding. That is, $s_{X1}$ is calculated based on $s_{Z1}$ and $s_{Y1}$, assuming that the following equation holds.

$$s_{X1} \cdot s_{Y1} \cdot s_{Z1} = 1 \quad (3)$$

With the above processing, $s_{X1}$, $s_{Y1}$, and $s_{Z1}$ are calculated for each of the regions defined by $z > z_M$ and $z \leq z_M$. A transformation matrix $T_{D1}$ describing affine transformation based on these scale factors is calculated for each of the regions defined by $z > z_M$ and $z \leq z_M$. In this case, a position coordinate vector $v_{SD1i\_DEV}$ representing the surface position 807 after compression deformation in the first step is calculated by $$v_{SD1i\_DEV} = v_{Si\_DEV} \cdot T_{D1} \quad (4)$$

FIG. 8B is a schematic view showing how deformation correction processing is performed as the second step in deformation estimation such that a position corresponding to a contact region at a surface position on the breast coincides with a position on the holding plate. FIG. 8B shows a surface position 810 after correction by elongation deformation of the surface position 807 after compression deformation using the position of the contact region. In this embodiment, as in the first step, the target region is processed after being divided into two regions defined by $z > z_M$ and $z \leq z_M$. Note, however, that in the processing in this step, transformations with different scalings are further respectively performed for line regions $L(x, y)$ in the z-axis direction at the respective positions $(x, y)$ in the target region. Assume that since the amount of deformation by this correction processing is not large, a change in volume can be neglected. That is, the volume is not stored before and after correction, and scaling is performed only in the z direction. That is, a scale factor $s_{Z2}(x, y)$ in the z-axis direction is obtained for each line region $L(x, y)$, and correction processing is performed based on the obtained scaling factor.

A case of $z > z_M$ will be described first. When the line region $L(x, y)$ intersects with the contact region 802, affine transformation is performed so as to apply scaling in the direction in which the z-coordinate ($z_{SD1}(x, y)$) of the surface position 807 on the line region L elongates so as to match the contact region 802 ($z = z_U$). That is, $s_{Z2}$ is obtained by $$s_{Z2}(x, y) = (z_U - z_M)/(z_{SD1}(x, y) - z_M) \text{ (if } z > z_M) \quad (5)$$

In addition, on all the line regions $L(x, y)$ which do not intersect with the contact region 802, the value of $s_{Z2}$ of the line region L intersecting with the lower end (the point of the contact region, whose y is minimum) of the contact region 802 on the same sagittal plane is used as $s_{Z2}(x, y)$. This makes it possible to implement seamless deformation correction between a line region which does not intersect with the contact region and a line region which intersects with the contact region.

The same processing as in the case of $z > z_M$ is performed for the case of $z \leq z_M$. That is, when the line region $L(x, y)$ intersects with a contact region 803, affine transformation is performed so as to apply scaling in the elongation direction in which the z-coordinate of the surface position 807 on the line region L matches the contact region 803 ($z = z_L$). That is, $s_{Z2}$ is obtained by $$s_{Z2}(x, y) = (z_L - z_M)/(z_{SD1}(x, y) - z_M) \text{ (if } z \leq z_M) \quad (6)$$

Note that processing to be performed when the line region L does not intersect with the contact region 803 is the same as that in the case of $z > z_M$, and hence a description of the processing will be omitted.

A transformation matrix $T_{D2}(x, y)$ describing affine transformation based on the calculated scale factors is calculated for each line region $L(x, y)$ in each of the regions defined by $z > z_M$ and $z \leq z_M$. In this case, a position coordinate vector $v_{SD2i\_DEV}$ representing the surface position 810 after elongation correction in the second step is calculated by $$v_{SD2i\_DEV} = v_{SD1i\_DEV} T_{D2}(x_i, y_i) \tag{7}$$

where $x_i$ and $y_i$ are the x- and y-coordinates of $v_{SD1i\_DEV}$.

FIG. 8C is a schematic view showing a state after deformation correction processing in the second step. As is obvious from FIG. 8C, the surface position 810 after elongation deformation is deformed to come into contact with the contact regions 802 and 803. Using the information of the contact regions between the breast and the holding plates for alignment can obtain a deformation result close to real compression deformation. With the above processing, the deformation function $F_{DEV}$ for an arbitrary coordinate is calculated as a combination of $T_{D1}$ and $T_{D2}$.

In the above manner, in this embodiment, the deformation function $F_{DEV}$ is calculated, which deforms the object by using affine transformation so as to make the object come into contact with the contact regions acquired in step S2050. However, the method of calculating the deformation function $F_{DEV}$ is not limited to this. The deformation function $F_{DEV}$ may be calculated by using a deformation technique generally used for nonrigid alignment, such as RBF (Radial Basis Function) or FFD (Free Form Deformation). For example, in deformation using RBF, the deformation function $F_{DEV}$ can be calculated, which deforms the overall object such that when combinations of a plurality of corresponding points are designated between the object before deformation and the object after deformation, the designated corresponding points match (almost match) each other. In this embodiment, therefore, combinations of corresponding points are generated among points on the surface position 801 (before deformation) in FIG. 8A and points on the contact regions 802 and 803 (after deformation), and the deformation function $F_{DEV}$ based on RBF is obtained.

First of all, a point $v_{Uj\_DEV}$ on the contact region 802 is designated as a point on the holding plane $P_U$ after deformation. As a point before deformation which corresponds to the point $v_{Uj\_DEV}$, a point $v_{Ui\_MRI}$ is obtained, at which a straight line which passes through the point $v_{Uj\_DEV}$ and is parallel to the z-axis (parallel to the compression direction 805) intersects with the surface position 801. Note, however, that the z-coordinate of the point $v_{Ui\_MRI}$ is larger than the holding plane $P_U$. A combination of the point $v_{Uj\_DEV}$ and the point $v_{Ui\_MRI}$ is obtained as a combination Acorres. A point $v_{Lj\_DEV}$ on the contact region 803 is designated as a point on the holding plane $P_L$ after deformation. Likewise, a point $v_{Li\_MRI}$ is obtained, at which a straight line which passes through the point $v_{Lj\_DEV}$ and is parallel to the z-axis (parallel to the compression direction 806) intersects with the surface position 801. Note, however, that the z-coordinate of the point $v_{Li\_MRI}$ is smaller than the holding plane $P_L$. A combination of the point $v_{Lj\_DEV}$ and the point $v_{Li\_MRI}$ is obtained as a combination Bcorres. Finally, the deformation function $F_{DEV}$ based on RBF is calculated so as to match the combinations Acorres and Bcorres of the corresponding points before deformation with those after deformation. This makes it possible to estimate compression deformation of the object so as to make the surface region before deformation (the surface position 801) come into contact with the contact regions 802 and 803 after deformation.

In addition, in this embodiment, the deformation of the object is calculated by using the two contact regions 802 and 803 on the holding planes $P_U$ and $P_L$. However, the deformation of the object may be calculated by using only one of the holding planes.

(Step S2070: Generation of Deformed MRI Image)

In step S2070, the deformed image generation unit 1080 generates a deformed MRI image aligned with a PAT image based on the MRI image 300 by using the deformation function $F_{DEV}$ obtained in step S2060. That is, the deformed image generation unit 1080 generates a deformed MRI image by deforming the MRI image 300 such that the breast shape in the MRI image 300 becomes the shape estimated in step S2060. First of all, the deformed image generation unit 1080 performs coordinate transformation from the three-dimensional coordinate position of each pixel constituting the MRI image 300 to a three-dimensional coordinate position in the PAT apparatus coordinate system $C_{DEV}$, and then performs deformation processing by using the deformation function $F_{DEV}$. The deformed image generation unit 1080 then generates a deformed MRI image in the PAT image coordinate system $C_{PAT}$ by performing coordinate transformation of the three-dimensional coordinate position of each pixel constituting the deformed MRI image by using the inverse matrix of the coordinate transformation matrix $T_{PtoD}$.

Figure 9A:
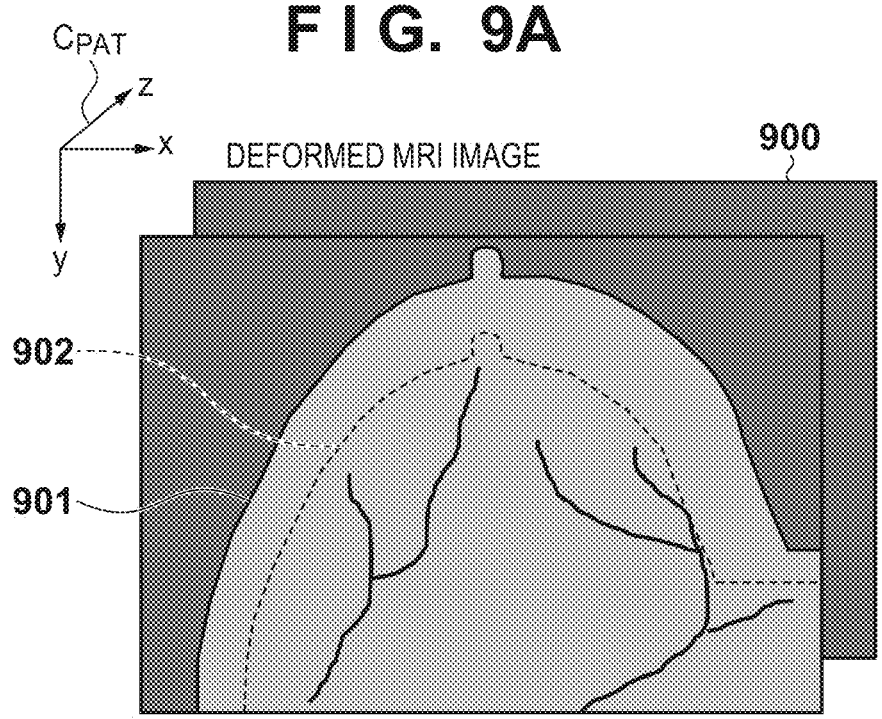
FIGS. 9A and 9B are schematic views each showing an MRI image after deformation.
Figure 9B:
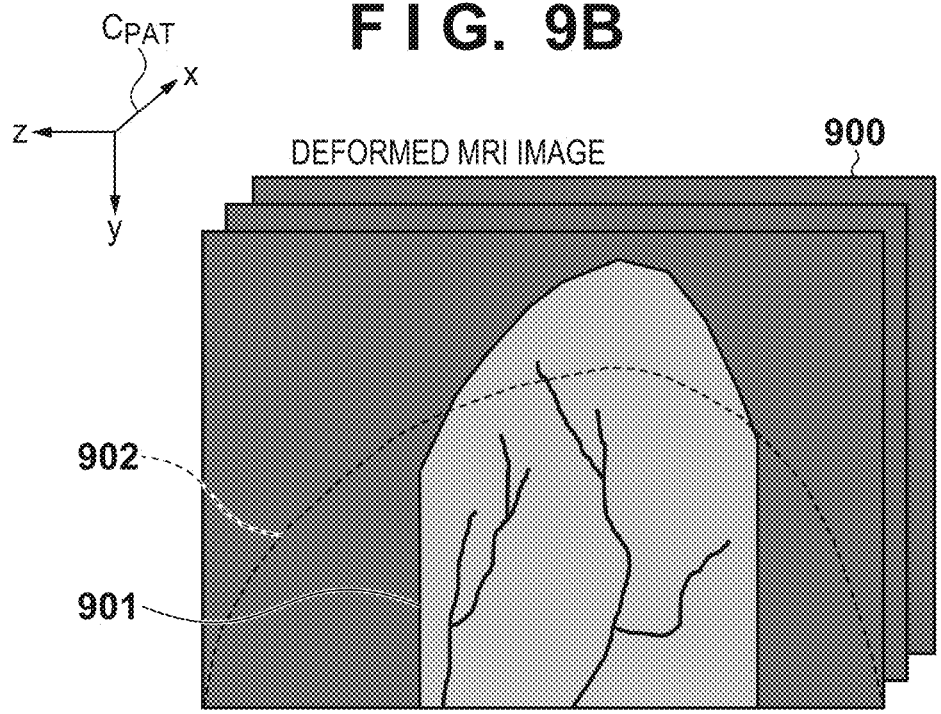

FIGS. 9A and 9B are schematic views each showing an MRI image after deformation (deformed MRI image). FIG. 9A is a schematic view showing a two-dimensional image obtained by slicing an MRI image after deformation along an axial slice. FIG. 9B is a schematic view showing a two-dimensional image obtained by slicing an MRI image after deformation along a sagittal slice. FIGS. 9A and 9B show a deformed MRI image 900, a breast region 901 after deformation, and a breast shape 902 before deformation. A comparison between the breast region 901 after deformation and the breast shape 902 before deformation indicates that compression in the z-axis direction of the PAT image coordinate system $C_{PAT}$ elongates the breast region on the x-y plane and compresses the region in the z-axis direction.

(Step S2080: Display of Deformed MRI Image and PAT Image)

Figure 10:
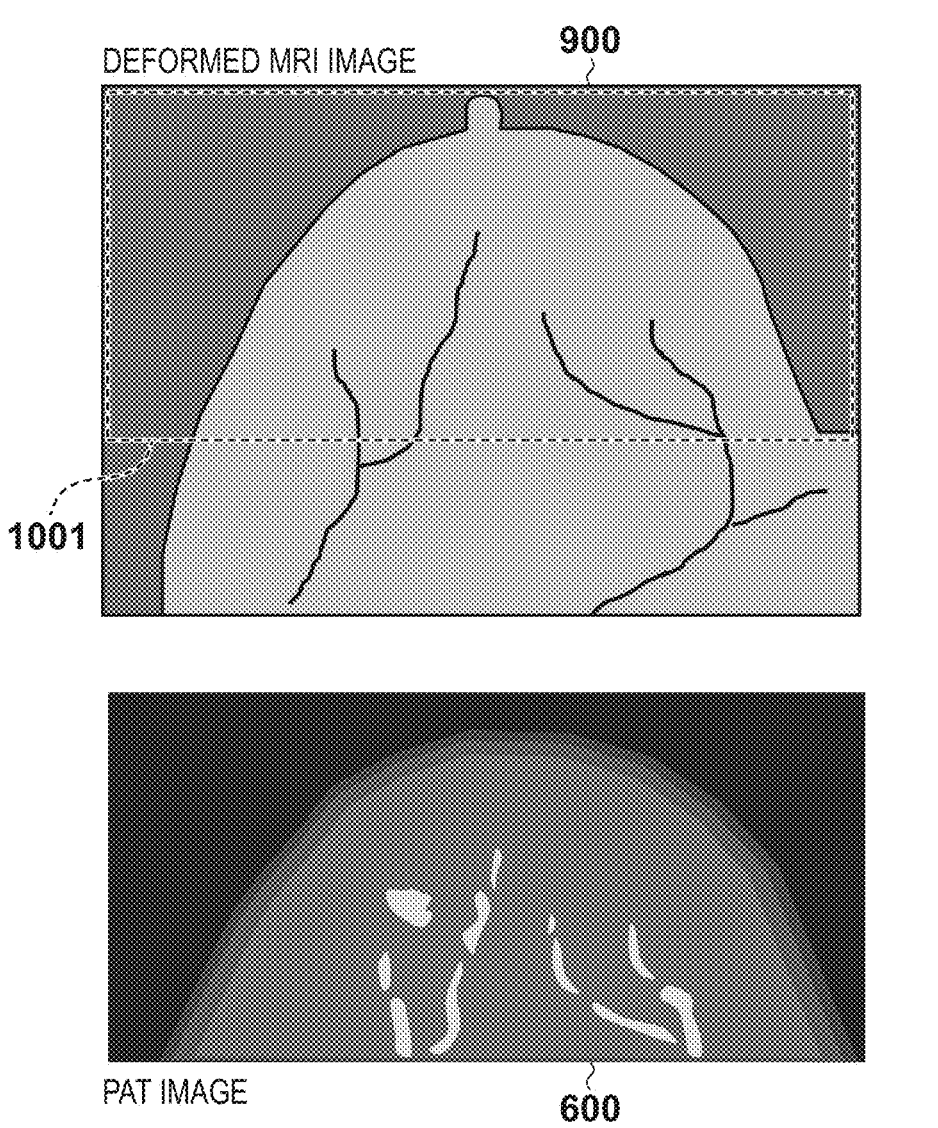
FIG. 10 is a view showing an example of a screen displaying a deformed MRI image and a PAT image.

In step S2080, the image display unit 1090 displays the deformed MRI image 900 generated in step S2070 and the PAT image 600 acquired in step S2020 on the monitor (not shown) side by side. FIG. 10 shows an example of a screen displaying the deformed MRI image and the PAT image. Referring to FIG. 10, the deformed MRI image 900 and the PAT image 600 on the same axial slice are displayed vertically side by side. In this case, a corresponding region 1001 is display information for indicating a region corresponding to the display region of the PAT image 600 to the user. Note that the display form of a deformed MRI image and a PAT image is not limited to any specific display form.

As described above, in this embodiment, the contact regions between an object and the holding plates which compress the object are detected from a camera image, and the three-dimensional position information of the regions is used for compression deformation alignment. This makes it possible to provide a mechanism for performing high-accuracy alignment between a PAT image and an MRI image.

Second Embodiment

The image processing apparatus according to the first embodiment generates a deformed MRI image by compression deformation using affine transformation. However, since compression deformation using affine transformation does not strictly simulate a real physical phenomenon, a considerable error may occur between simulated compression deformation and compression deformation caused at the time of actually capturing a PAT image. In this embodiment, therefore, based on the information of contact regions between the breast and the holding plates, the deformation of an object is estimated by using a physical deformation simulation technique of simulating a real physical phenomenon, and a deformed MRI image is generated by applying compression deformation to an MRI image. This implements more accurate alignment between the PAT image and the MRI image, thereby improving the efficiency of diagnosis using both the images. The image processing apparatus according to this embodiment will be described mainly about differences from the first embodiment. The arrangement of a system according to this embodiment is the same as that of the first embodiment. However, only the operation of a deformation estimation unit 1070 differs from that in the first embodiment.

Figure 11:
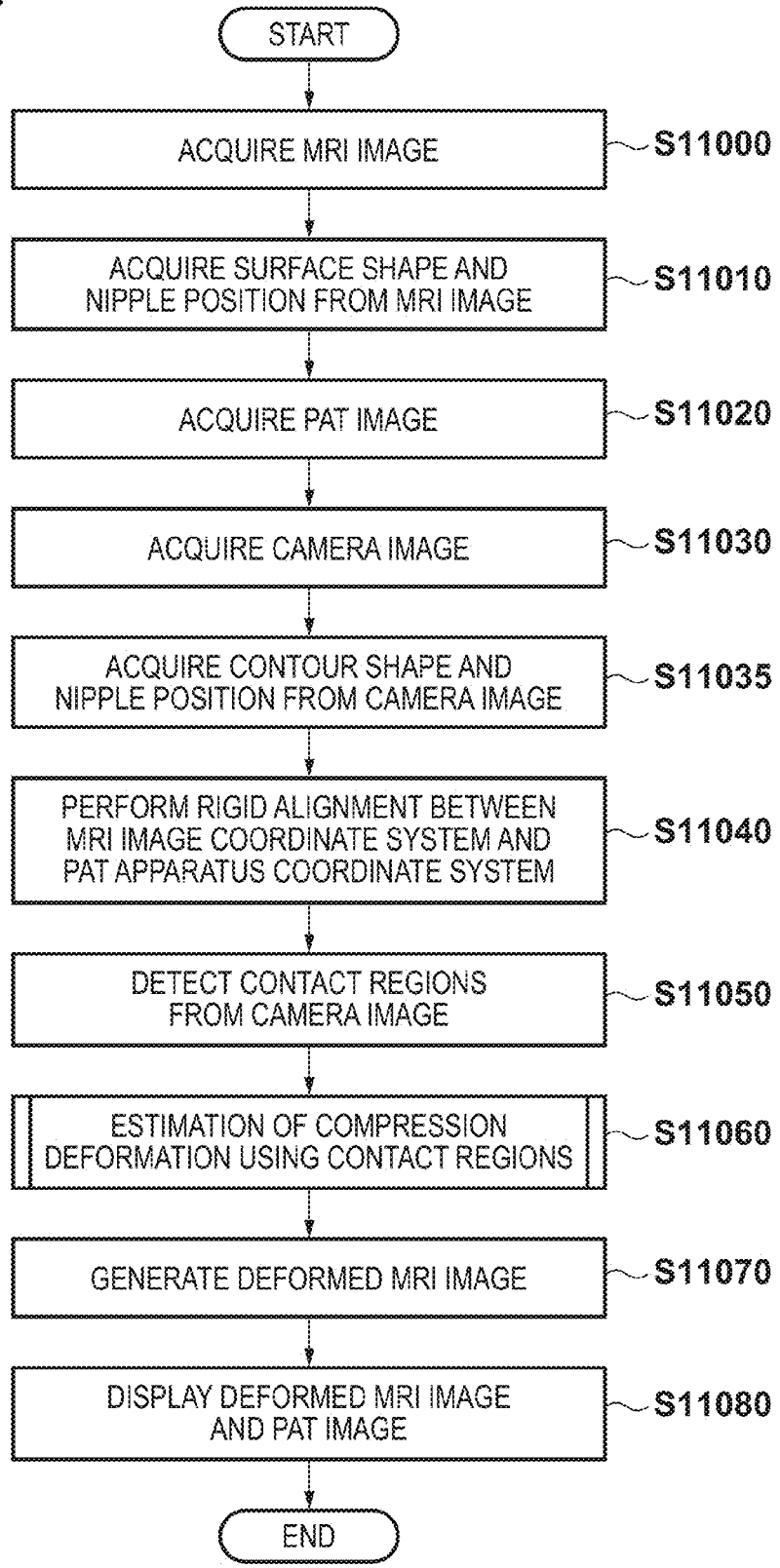
FIG. 11 is a flowchart showing the processing performed by the image processing apparatus 100.

The operation and processing procedure of each unit of an image processing apparatus 100 according to this embodiment will be described next with reference to the flowchart shown in FIG. 11. Since processing in steps S11000 to S11050 and processing in steps S17070 and S17080 are the same as those in steps S2000 to S2050 and in steps S2070 and S2080 in the first embodiment, a description of the processing will be omitted. Therefore, only processing in step S11060 will be described in detail below.

(Step S11060: Estimation of Compression Deformation Using Contact Regions)

In step S11060, the deformation estimation unit 1070 estimates the surface shape of the breast after compression deformation from the surface shape of the breast obtained from the MRI image by a physical deformation simulation using the contact area information acquired in step S11050 as constraints. More specifically, physical deformation simulations are performed while deformation parameters are variously changed to obtain a deformed shape which minimizes an evaluation value representing the appropriateness of deformation. In this case, the deformation estimation unit 1070 in this embodiment has a feature that an evaluation value is defined in consideration of the degree of matching between calculated contact regions obtained from the generated deformed shape and the contact regions acquired in step S11050. That is, the deformed shape into which the breast shape obtained from the MRI image is to be compressed/deformed is estimated so as to almost match the contact regions between the breast and the holding plates. The details of processing in this step will be described with reference to the flowchart of FIG. 12.

(Step S12000)

In step S12000, the deformation estimation unit 1070 generates a three-dimensional mesh (to be referred to as a mesh M hereinafter) representing the surface shape based on the surface shape of the breast acquired in step S11010. First of all, the deformation estimation unit 1070 obtains a position coordinate vector $v_{Si\_DEV}$ of a surface position 801 in a PAT apparatus coordinate system $C_{DEV}$ by the same method as that in the first embodiment. An inner region of the breast is then discriminated based on the surface position 801, and the mesh M is arranged in the inner region.

Figure 13A:
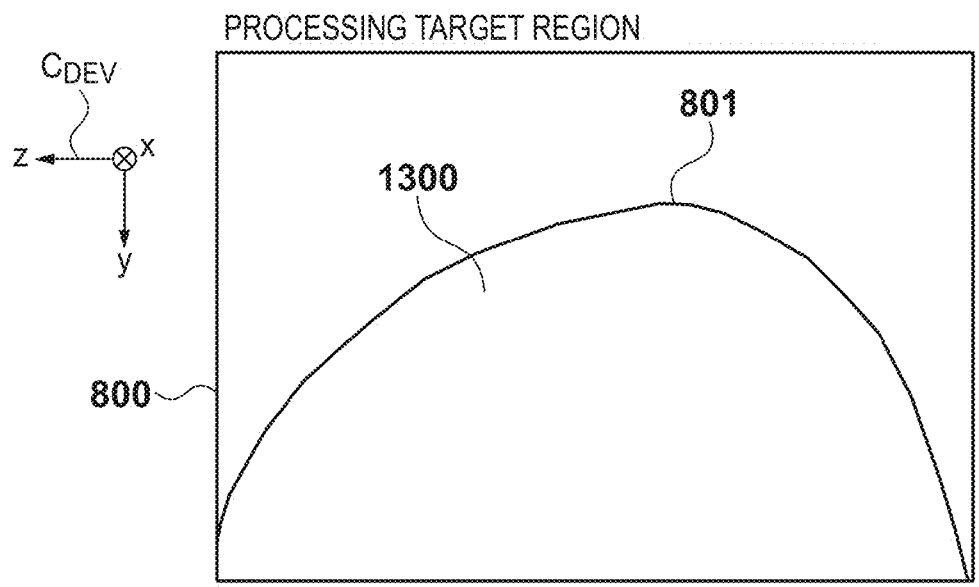
FIGS. 13A and 13B are schematic views showing a method of generating a mesh M.
Figure 13B:
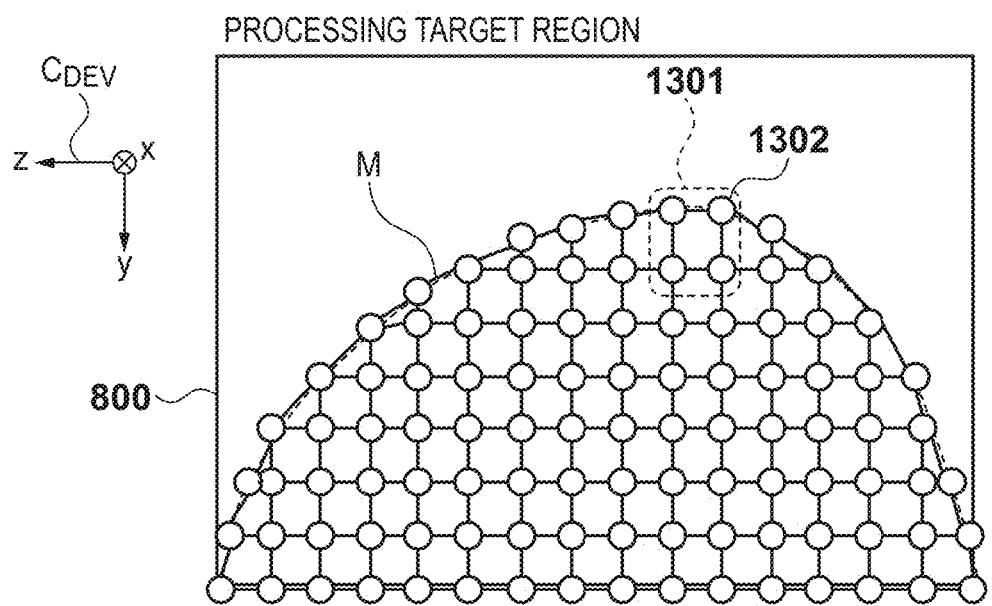

FIGS. 13A and 13B are schematic views showing a method of generating the mesh M. FIG. 13A is a sagittal slice of a processing target region 800 of the breast, and shows the surface position 801 of the breast on the slice and a corresponding inner region 1300. FIG. 13B is a schematic view showing the arranged mesh M. As shown in FIG. 13B, the mesh M is generated by arranging mesh elements 1301 as three-dimensional structures such as hexahedrons or tetrahedrons in the inner region 1300 of the breast. The mesh M is described by the positions of vertices (nodes 1302) of these mesh elements and concatenation information. In the following description, the number of nodes of the mesh M which are arranged by processing in this step is represented by $n_m$, and the position of each node is represented by $s_l$ ($1 \le l \le n_m$). Since a displacement field in the elements can be expressed by the displacement of each node, it is possible to obtain the displacement of an arbitrary point in the breast based on this displacement.

(Step S12010)

In step S12010, the deformation estimation unit 1070 generates $n_p$ combinations of deformation parameters $p_k$ ($1 \le k \le n_p$) by combining values which the respective components (Young's moduli, Poisson ratios, and the like) of deformation parameters can take. For example, the deformation estimation unit 1070 generates the deformation parameters $p_k$ by dividing the range which each component can take at proper intervals and obtaining all combinations of divided ranges.

According to non-patent literature 3, in order to cope with the anisotropy of hardness of a breast, a Young's modulus at a coronal plane (x-z plane) of the human body and a Young's modulus ratio (defined as $p_y$) in the anteroposterior direction of the human body are used as material parameters in a physical deformation simulation. This embodiment also uses the Young's modulus ratio $p_y$ as a deformation parameter. For example, the deformation estimation unit 1070 generates $n_p=25$ combinations of deformation parameters as combinations of $p_y=1, 2, 3, 4$, and 5, and $p_p=0.0, 0.2, 0.4, 0.45$, and 0.499 as values which the Young's modulus ratio $p_y$ and a Poisson ratio $p_p$ as components of the deformation parameter $p_k$ can take.

(Step S12020)

In step S12020, the deformation estimation unit 1070 initializes a loop variable k to 1.

(Step S12030)

In step S12030, the deformation estimation unit 1070 obtains a deformed mesh $DM_k$ as a mesh after deformation by performing a physical deformation simulation based on the finite element method with respect to the mesh M using (assuming) the kth deformation parameter $p_k$.

Figure 14A:
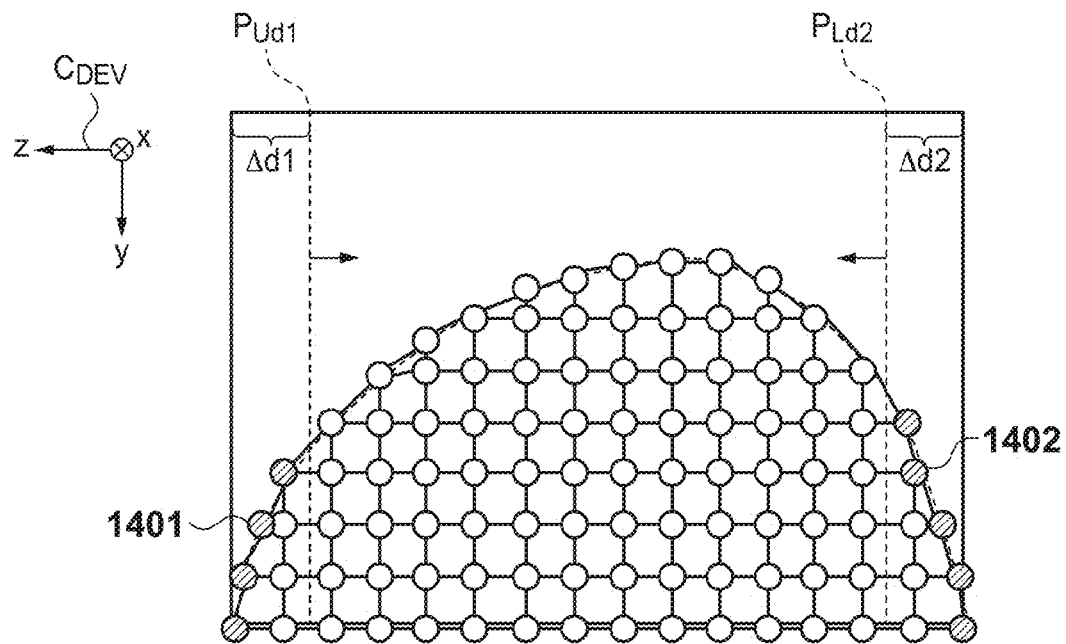
FIGS. 14A and 14B are views for explaining a compression deformation simulation.
Figure 14B:
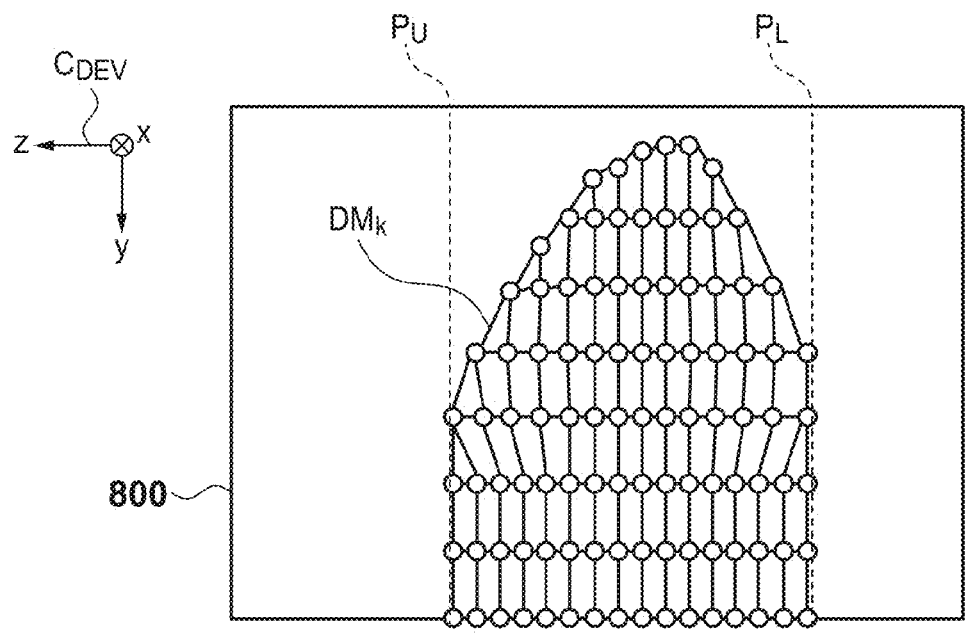

A compression deformation simulation using holding plates as a physical deformation simulation performed in this step will be specifically described below with reference to FIGS. 14A and 14B. In actual compression deformation using the holding plates, when the two holding plates are moved to the center of the breast by distances $\Delta d_1$ and $\Delta d_2$, respectively, the surface regions of the breast which protrude outside the holding plates after the movement stick to the holding plates. Assume that the two holding plates are moved by $\Delta d_1$ and $\Delta d_2$, respectively, as shown in FIG. 14A. The deformation estimation unit 1070 then obtains nodes (outside surface nodes 1401 and 1402) protruding outside holding planes $P_{Ud1}$ and $P_{Ld2}$ from nodes (surface nodes) representing the body surface of the nodes 1302 of the mesh M. The deformation estimation unit 1070 then obtains displacement amounts for making the outside surface nodes 1401 and 1402 come into contact with the holding planes, respectively. The deformation estimation unit 1070 executes a calculation based on the finite element method by providing these displacement amounts as boundary conditions C for a deformation simulation, and moves the two holding plates by $\Delta d_1$ and $\Delta d_2$ to deform the mesh, thereby generating a deformed mesh. In this embodiment, the interval during which the two holding plates are moved to final holding positions $P_U$ and $P_L$ is divided into n deformation simulations to cope with changes in boundary conditions which occur in the process of deformation. FIG. 14B shows the deformed mesh $DM_k$ as a result of repeating n deformation simulations. It is obvious from FIG. 14B that the deformed mesh of the breast is compressed in the z-axis direction and elongated in the y-axis direction between the holding positions $P_U$ and $P_L$ by physical deformation simulations.

(Step S12040)

In step S12040, based on the contact region information acquired in step S11050, the deformation estimation unit 1070 calculates an evaluation value $E_k$ of the appropriateness of the shape of the deformed mesh $DM_k$ (the appropriateness of the deformation represented by $DM_k$) obtained in step S12030. For example, the deformation estimation unit 1070 calculates, as the evaluation value $E_k$, the shape error between the calculated contact regions obtained from the deformed mesh $DM_k$ and the contact regions acquired in step S11050.

FIGS. 15A and 15B are schematic views showing the positional relationship between contact regions and a deformed mesh. FIG. 15A is a view showing the contact regions and the deformed mesh $DM_k$ on a sagittal slice of the processing target region 800. In this case, of the nodes belonging to the deformed mesh $DM_k$, nodes (to be referred to as contact nodes hereinafter) 1500 and 1501 come into contact with the holding planes. That is, the contact nodes represent calculated contact regions based on the deformed mesh $DM_k$. FIG. 15B is a view showing the contact region and the deformed mesh $DM_k$ on an axial slice ($z=z_U$) 1502 on the plane $P_U$ of the processing target region 800. A contact region 802 located on the holding plane and the contact node 1500 are shown on the axial slice 1502. As is obvious from FIG. 15B, there is an offset (to be referred to as an offset region 1503 hereinafter) between the contact region 802 and the contact node 1500 (that is, between the measured contact region and the calculated contact region). In this embodiment, a shape error $E_{Uk}$ on the holding plane $P_U$ is calculated as the absolute value of the difference between an area $S_{CU}$ of the contact region 802 and an area $S_{Uk}$ of the region formed from the contact node 1500, as indicated by equation (8) given below:

$$E_{Uk}=|S_{CU}-S_{Uk}| \quad (8)$$

Likewise, a shape error $E_{Lk}$ on the holding plane $P_L$ is calculated by using an area $S_{CL}$ of a contact region 803 and an area $S_{Lk}$ of the region formed from the contact node 1501 according to equation (9) given below:

$$E_{Lk}=|S_{CL}-S_{Lk}| \quad (9)$$

The evaluation value $E_k$ of the deformed shape is then calculated as the sum of these errors according to equation (10):

$$E_k=E_{Uk}+E_{Lk} \quad (10)$$

Note, however, that the method of calculating the evaluation value $E_k$ based on contact regions is not limited to the above method. For example, as the degree of matching between a set of the contact region 802 and the contact region 803 (the acquired three-dimensional position information of the contact regions) and a set of the region formed from the contact node 1500 and the region formed from the contact node 1501 (the three-dimensional position information of the calculate contact regions), the degree of overlap between these regions may be evaluated. For example, a Jaccard coefficient may be obtained, and its reciprocal may be used as $E_k$. Alternatively, any one of the methods of measuring the degree of matching between regions may be used. In addition, the evaluation value $E_k$ may be obtained based on the degree of matching between the contact regions projected on outer appearance images instead of the contact regions in a three-dimensional space. For this purpose, first of all, the contact nodes 1500 and 1501 are projected and transformed into nodes in the front camera image coordinate system and the rear camera image coordinate system, respectively, to obtain calculated contact regions on the respective outer appearance images (the regions obtained by projecting the calculated contact regions onto two-dimensional images). The degree of matching between the calculated contact region and the contact region on the same image obtained in step S11050 is obtained as the evaluation value $E_k$. In this case, it is possible to use, as the degree of matching between the contact regions, for example, a difference $E_{2D\_Ck}$ between the area of a calculated contact region on an outer appearance image and the area of a contact region detected on the outer appearance image. In addition, it is possible to evaluate the degree of matching based on the degree of overlap between the calculated contact region on the outer appearance image and the contact region detected on the outer appearance image (the two-dimensional position information of the acquired contact region). For example, the reciprocal of a Jaccard coefficient between these two regions may be used as an evaluation value. This makes it possible to estimate a deformed shape such that the calculated contact region on the outer appearance image almost matches the two-dimensional position information of the contact region acquired from the outer appearance image.

In addition, the calculation of the evaluation value $E_k$ need not be based on only contact region information, and may use both contact region information and other observation information concerning shapes (for example, the outer contour of the breast and the position of the nipple, which are depicted in an outer appearance image). For example, this calculation may be performed in consideration of a shape error $E_{2D\_Sk}$ between the shape of the outer contour (silhouette) of the breast depicted in an outer appearance image and the shape of the outer contour of the deformed mesh $DM_k$ projected on the outer appearance image. In addition, the calculation may be performed in consideration of a distance error $E_{2D\_Fk}$ between a feature point (for example, a nipple position) of the breast depicted in an outer appearance image and a corresponding feature point of the deformed mesh $DM_k$ projected on the outer appearance image. If, for example, the value obtained by synthesizing the errors $E_{2D\_Ck}$, $E_{2D\_Sk}$, and $E_{2D\_Fk}$ is used as the evaluation value $E_k$, $E_k$ can be represented by $$E_k=a \cdot E_{2D\_Ck}+b \cdot E_{2D\_Sk}+c \cdot E_{2D\_Fk} \quad (11)$$

where a, b, and c are weight coefficients, and a+b+c=1 holds. Obviously, the evaluation value $E_k$ may be the value obtained by combining the evaluation value obtained by equation (10) given above and $E_{2D\_Sk}$ and $E_{2D\_Fk}$. With the above processing, the evaluation value $E_k$ of the appropriateness of the shape of the deformed mesh $DM_k$ is calculated.

(Step S12050)

In step S12050, a deformation estimation unit 1070 determines whether the evaluation value $E_k$ calculated in step S12040 is smaller than a minimum value $E_{MIN}$ of the current evaluation value. If $E_k<E_{MIN}$, the process advances to step S12060. If $E_k \geq E_{MIN}$, the process advances to step S12070.

(Step S12060)

In step S12060, the deformation estimation unit 1070 updates the minimum value $E_{MIN}$ of the current evaluation value to $E_k$ ($E_{MIN}=E_k$), and further updates a deformed mesh $DM_{MIN}$ corresponding to $E_{MIN}$ to $DM_k$ ($DM_{MIN}=DM_k$).

(Step S12070)

In step S12070, the deformation estimation unit 1070 updates the loop variable k to (k+1) (k=k+1).

(Step S12080)

In step S12080, the deformation estimation unit 1070 determines whether the loop variable k is larger than a number $n_p$ of deformation parameters $p_k$. If $k>n_p$, the process advances to step S11070. If $k \leq n_p$, the process advances to step S12030.

With the above operation, the processing performed by the deformation estimation unit 1070 in step S11060 is terminated. Executing the above processing procedure will acquire the deformed mesh $DM_{MIN}$ which minimizes the evaluation value $E_k$ of the appropriateness of the shape among the results obtained by executing deformation simulations assuming various deformation parameters $p_k$. At this time, a deformation function F(x, y, z) is acquired as a displacement vector $d_{MIN\_l}$ ($1 \leq l \leq n_m$) which gives displacement to each node from the mesh M to the deformed mesh $DM_{MIN}$.

As described above, in this embodiment, an MRI image having undergone compression deformation to almost match the contact regions between the breast and the holding plates is generated by using a physical deformation simulation of simulating a real physical phenomenon. This makes it possible to implement high-accuracy alignment between a PAT image and an MRI image and improve the efficiency of diagnosis using both the images.

Modification of Second Embodiment

The holding plates of the PAT apparatus 120 according to this embodiment are flat plates, and the holding surfaces which hold a breast are planes. However, the shapes of the holding surfaces are not limited to planes, and the holding surfaces may have any known existing shapes. For example, each holding surface may be obtained by combining two planes or have an arcuated shape. In this case, in step S11050, the three-dimensional position of a contact region may be calculated as an intersection point between the holding surface having one of such known shapes and a visual line to each point of the contact region on an outer appearance image.

In addition, the apparatus need not be configured to store the shape of each holding surface as known information in advance, and may be configured to measure the deformed shape of each holding surface by a different method in each case. In a PAT apparatus, in order to receive ultrasonic signals, gel-like members are sometimes bonded to the holding plates, and a breast as an object is held by the holding plates through the gel-like members so as to prevent air from existing between the ultrasonic prove and the breast. In this case, if the surface shape of each gel-like member on which the breast is held has been measured by an ultrasonic image sensing device or the like, the three-dimensional shape of the gel-like member is known. If, therefore, the contact regions between the gel-like members and the breast can be detected from a camera image, the three-dimensional position information of the contact regions can be obtained by using the three-dimensional shapes of the gel-like members and can be used for compression deformation alignment. In compression deformation alignment in this case, however, it is necessary to perform a physical deformation simulation in consideration of not only the breast but also the gel-like members. This operation can be executed by, for example, generating meshes (to be referred to as gel meshes) based on material coefficients having the characteristics of the gel-like members using a conventional finite element method, and performing a compression deformation simulation based on the two holding plates including the gel meshes and a breast mesh.

Third Embodiment

In the first and second embodiments, in order to perform deformation alignment between a PAT image and an MRI image, a deformed MRI image is generated by applying compression deformation to the MRI image based on the information of the contact regions between the breast and the holding plates. In contrast to this, an image processing apparatus according to the third embodiment is aimed at accurately acquiring the three-dimensional shape of a breast as an object of a PAT apparatus. The apparatus is also aimed at improving the accuracy of estimation of a light amount distribution in a breast, based on the measured three-dimensional shape of the breast, and accurately imaging a light absorption coefficient distribution in the breast. In addition, the apparatus is aimed at accurately imaging the distribution of the degrees of oxygen saturation of blood. In this embodiment, the apparatus obtains a three-dimensional shape model approximating the shape of a breast in an upheld state, and generates a three-dimensional shape model after deformation by applying compression deformation to the three-dimensional shape model so as to match the contact regions between the breast and the holding plates. The apparatus then accurately images the distribution of the light absorption coefficients and the distribution of the degrees of oxygen saturation of blood in the breast based on the generated three-dimensional shape model. A system according to the embodiment will be described below.

Figure 16:
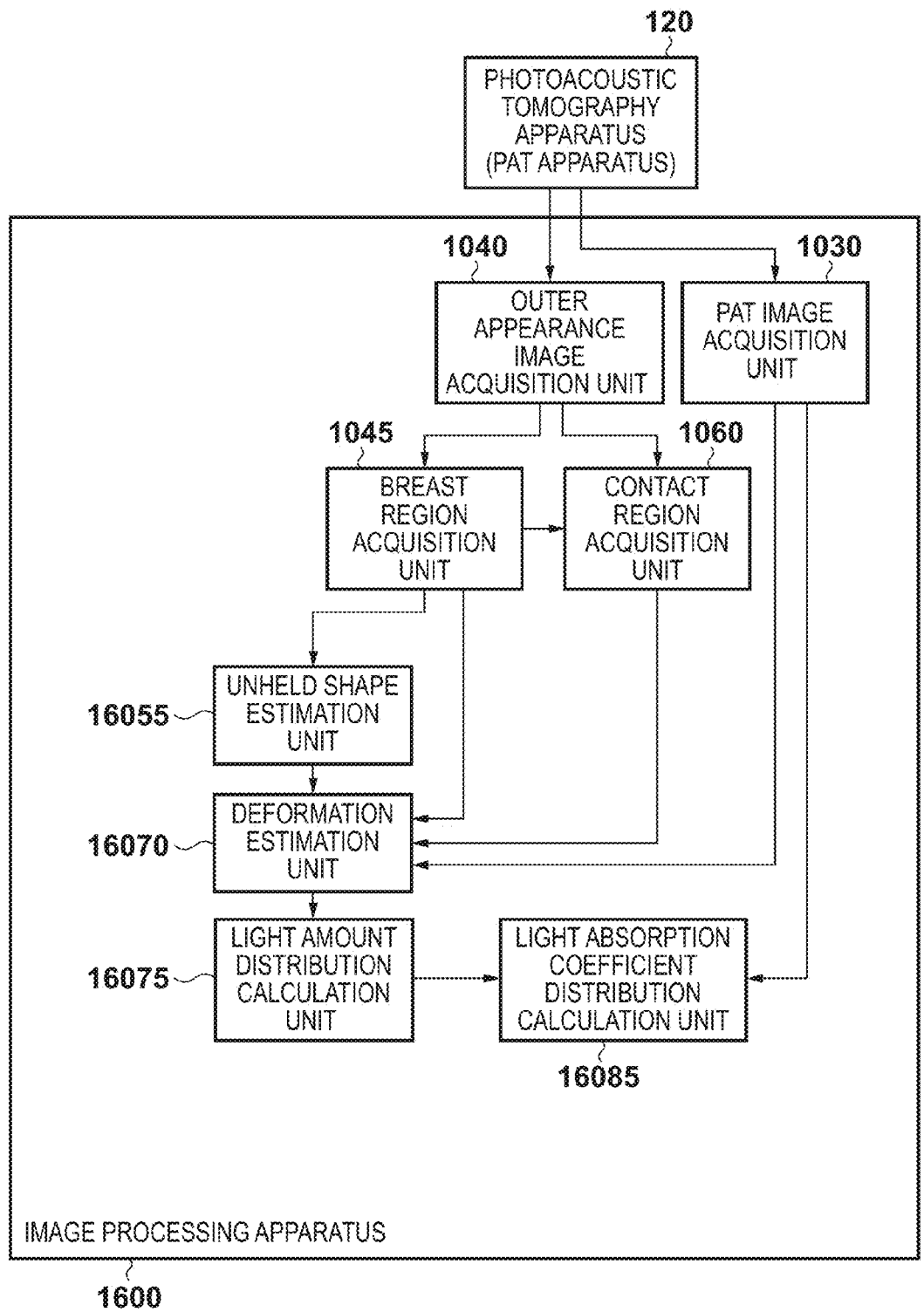
FIG. 16 is a block diagram showing an example of the functional arrangement of a system.

An example of the functional arrangement of the system according to this embodiment will be described first with reference to the block diagram of FIG. 16. As shown in FIG. 16, the system according to this embodiment includes an image processing apparatus 1600 and a PAT apparatus 120, which are connected to perform data communication with each other. The same reference numerals as in FIG. 1 denote the same functional units in FIG. 16, and a description of the functional units will be omitted.

In this case, the PAT apparatus 120 according to this embodiment includes two types of irradiation light having predetermined wavelengths (to be written as $\lambda 1$ and $\lambda 2$ hereinafter), and performs measurement using each irradiation light. The apparatus generates, as PAT images, three-dimensional images (to be referred to as optical energy deposition amount distribution images $D_{ACM\_\lambda 1}$ and $D_{ACM\_\lambda 2}$ hereinafter) by imaging optical energy deposition amount distributions in the breast with respect to the respective types of irradiation light.

Figure 17:
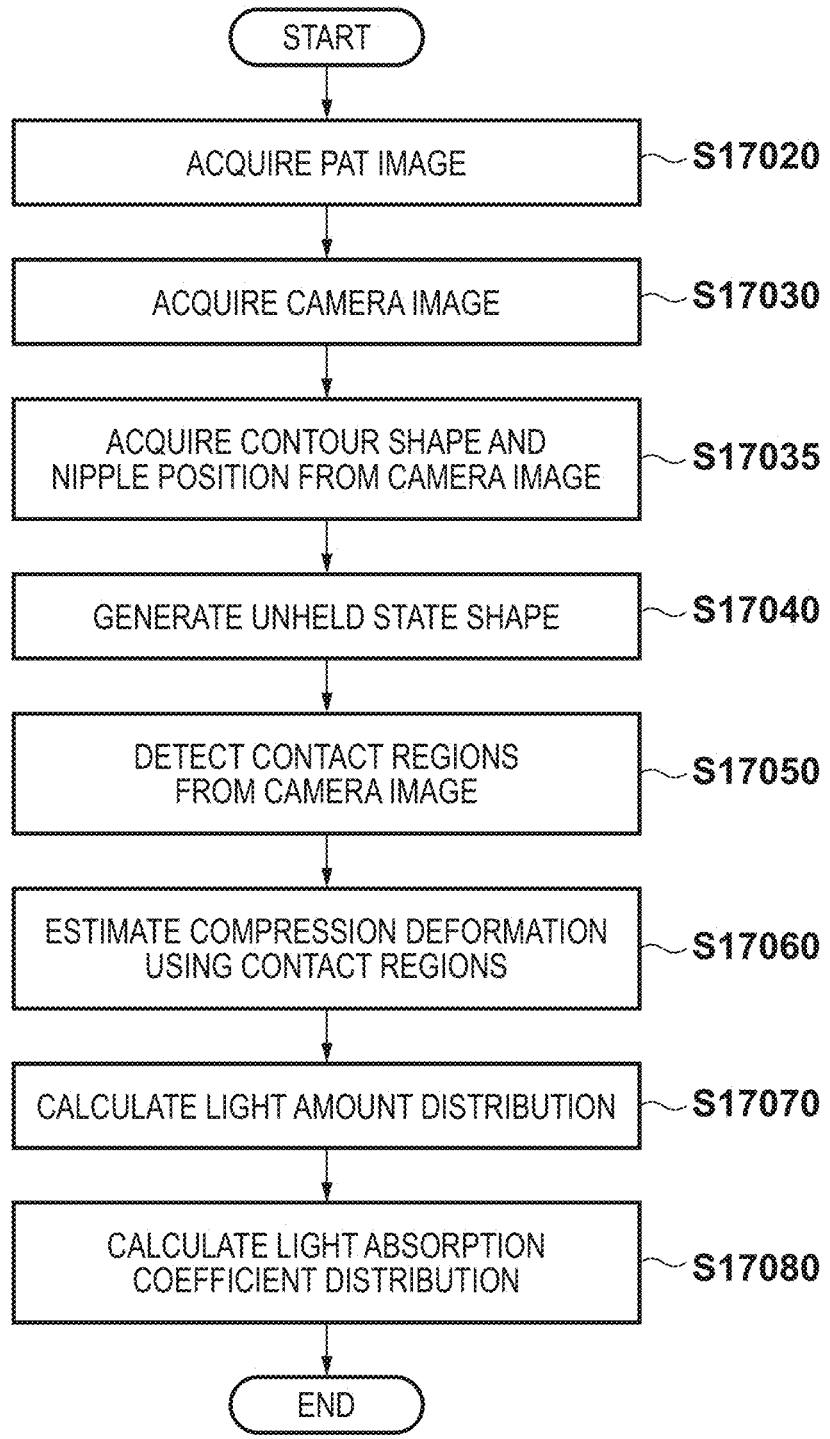
FIG. 17 is a flowchart showing the processing performed by an image processing apparatus 1600.

The operation and processing procedure of each unit of the image processing apparatus 1600 in this embodiment will be described next with reference to the flowchart of FIG. 17. Note, however, that processing in steps S17020, S17030, S17035, and S17050 is the same as that in steps S11020, S11030, S11035, and S11050 in the flowchart of FIG. 11, and hence a description of the processing will be omitted. Note that in step S17020, a PAT image acquisition unit 1030 in this embodiment acquires the optical energy deposition amount distribution images $D_{ACM\_\lambda 1}$ and $D_{ACM\_\lambda 2}$ with respect to two types of irradiation light as PAT images.

(Step S17040: Estimation of Unheld Shape)

In step S17070, an unheld shape estimation unit 16055 estimates the three-dimensional shape of the breast in an unheld state based on breast regions on camera images ($I'_{CAM1}$ and $I'_{CAM2}$) in an unheld state which are obtained in step S17035. For example, a shape model approximating the shape of the breast in an unheld state is generated by applying an ellipsoidal model (obtaining parameters which minimize the difference between a projection image of the model and the breast region).

(Step S17060: Estimation of Deformation)

In step S17060, a deformation estimation unit 16070 estimates the deformation of the breast by the same processing as that in step S11060 in the second embodiment, and generates a shape model of the breast (that is, a deformed mesh $DM_{MIN}$) in a held state. However, the processing in this embodiment differs from that in step S11060 in that the shape model obtained in step S17040 is used as a shape before deformation instead of the surface shape of the breast obtained from an MRI image.

(Step S17070: Calculation of Light Amount Distributions)

In step S17070, a light amount distribution calculation unit 16075 estimates light amount distributions $D_{LV\_\lambda 1}$ and $D_{LV\_\lambda 2}$ of the respective types of irradiation light applied in the breast based on the deformed mesh $DM_{MIN}$ acquired in step S17060. A light amount distribution is the three-dimensional distribution of irradiation light amounts in an inner region of the breast. When calculating a light amount distribution, the light amount distribution calculation unit 16075 requires information concerning incident light (light irradiation conditions), the three-dimensional shape of the breast, and optical coefficients (optical characteristic values) concerning light absorption and light scattering inside the breast. Assume that in this embodiment, a memory (not shown) in an image processing apparatus 100 holds information concerning incident light as known information. Assume also that the memory (not shown) in the image processing apparatus 100 holds average optical coefficients inside the breast, that is, average optical coefficients unique to a measurement region of the breast, as optical coefficients concerning the breast as known information. As the three-dimensional shape of the breast, the deformed mesh $DM_{MIN}$ acquired in step S17060 is used. The estimation of light amount distributions based on these pieces of information can be performed by, for example, the method disclosed in patent literature 1.

(Step S17080: Calculation of Light Absorption Coefficient Distributions)

In step S17080, a light absorption coefficient distribution calculation unit 16085 performs light distribution correction processing based on the light amount distributions obtained in step S17070 with respect to the optical energy deposition amount distribution images obtained in step S17020. With this correction processing, the light absorption coefficient distribution calculation unit 16085 generates three-dimensional images (to be referred to as light absorption coefficient distribution images $D_{ABS\_\lambda 1}$ and $D_{ABS\_\lambda 2}$ hereinafter) by imaging light absorption coefficient distributions in the object with respect to the respective wavelengths. That is, the light absorption coefficient distribution calculation unit 16085 calculates $D_{ABS\_\lambda 1}$ and $D_{ABS\_\lambda 2}$ by respectively dividing the optical energy deposition amount distribution images $D_{ACM\_\lambda 1}$ and $D_{ACM\_\lambda 2}$ by the light amount distributions $D_{LV\_\lambda 1}$ and $D_{LV\_\lambda 2}$.

It is possible to image the density distribution of substances constituting the living tissue by comparing the obtained light absorption coefficient distribution images $D_{ABS\_\lambda 1}$ and $D_{ABS\_\lambda 2}$ corresponding to the two types of wavelengths with the wavelength dependences unique to the substances constituting the living tissue. As substances constituting the living tissue, glucose, collagen, redox hemoglobin, and the like are expected.

As described above, in this embodiment, the three-dimensional shape model of the breast at the time of capturing a PAT image is generated based on the contact regions between the breast and the holding plates. This makes it possible to obtain accurate light amount distributions in the breast and implement high-accuracy estimation of light absorption coefficient distributions in the breast.

Modification of Third Embodiment

In this embodiment, the three-dimensional shape model of the breast in a held state is obtained by performing deformation processing for a three-dimensional shape model approximating the shape of the breast in an upheld state. However, a different method may be used. For example, the three-dimensional shape model of the breast in a held state may be directly generated (that is, may be generated without going through compression deformation estimation processing for the shape of the breast in an upheld state). For example, this processing may be performed as follows.

First of all, an ellipsoidal model satisfying (closest to) the following two conditions is generated, excluding the condition that the breast should exist inside the region sandwiched between the planes of the two holding plates (that is, the breast may protrude outside the region sandwiched between the planes of the holding plates):

The surface position of the ellipsoidal model should be in contact with the contours of the contact regions on the two holding plates.

When the ellipsoidal model is projected onto an outer appearance image, the silhouette shape of the projected ellipsoidal model should match the silhouette shape of the object (breast) depicted in each of the outer appearance images captured by the front and rear cameras.

Subsequently, a three-dimensional shape is generated by cutting off the regions of the ellipsoidal model which protrude outside the region sandwiched between the planes of the two holding plates. This makes it possible to generate a three-dimensional shape model matching the contact regions without going through compression deformation estimation processing.

Fourth Embodiment

Each functional unit constituting the image processing apparatus 100 (1600) shown in FIGS. 1 and 16 may be implemented by hardware. However, some or all of the functions may be implemented by software (computer programs).

When, for example, each functional unit constituting the image processing apparatus 100 (1600) is to be implemented by a computer program, consider an apparatus including a memory holding such computer programs and a processor which executes the computer programs. The processor of this apparatus can implement the function of each functional unit by executing a corresponding computer program stored in the memory. Therefore, such an apparatus can be applied to the image processing apparatus 100 (1600).

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest in so as to encompass all such modifications and equivalent structures and functions.

This application claims the benefit of Japanese Patent Application No. 2013-166992, filed Aug. 9, 2013 which is hereby incorporated by reference herein in its entirety.

What is claimed is:

1. An image processing apparatus comprising:
an acquisition unit configured to acquire position information of a contact region between an object and a holding member based on an image obtained by imaging the object in a held state in which the object is held by the holding member; and
an estimation unit configured to estimate a three-dimensional shape of the object in the held state based on the position information of the contact region,
wherein the image includes a two-dimensional image,
wherein the acquisition unit is configured to acquire two-dimensional position information of the contact region in the two-dimensional image,
wherein the estimation unit is configured to estimate the three-dimensional shape such that two-dimensional position information of a region obtained by projecting a calculated contact region contacting the holding member onto the two-dimensional image corresponds to the two-dimensional position information of the contact region acquired by the acquisition unit, and
wherein one or more of the acquisition unit or the estimation unit are implemented by a processor and a memory.

2. The apparatus according to claim 1, further comprising a shape acquisition unit configured to acquire a three-dimensional shape model of the object before contact with the holding member,
wherein the estimation unit is configured to estimate the three-dimensional shape of the object by deforming the shape model based on the position information of the contact region.

3. The apparatus according to claim 2, wherein the shape acquisition unit is configured to acquire the shape model based on a surface shape of the object which is obtained from a three-dimensional medical image of the object.

4. The apparatus according to claim 3, further comprising a unit configured to generate a deformed three-dimensional medical image by performing deformation processing for the three-dimensional medical image of the object so as to make the object have a shape estimated by the estimation unit.

5. The apparatus according to claim 1, wherein the holding member comprises a member being optically transmissive, and the image comprises an image obtained by imaging the object through the holding member.

6. The apparatus according to claim 1,
wherein the acquisition unit is configured to extract information concerning the contact region based on a luminance value of an object depicted in the image.

7. The apparatus according to claim 1, further comprising:
a photoacoustic image acquisition unit configured to acquire a photoacoustic image obtained by imaging the object in the held state;
a medical image acquisition unit configured to acquire a medical image;
a unit configured to acquire a deformed medical image by deforming the medical image based on the three-dimensional shape estimated by the estimation unit; and
a unit configured to cause a display unit to display the photoacoustic image and the deformed medical image.

8. The apparatus according to claim 7, wherein the medical image acquisition unit is configured to acquire an MRI image as the medical image.

9. The apparatus according to claim 1, further comprising:
a photoacoustic image acquisition unit configured to acquire a photoacoustic image obtained by imaging the object in the held state;
a light amount distribution acquisition unit configured to acquire a light amount distribution based on the three-dimensional shape estimated by the estimation unit, the light amount distribution being a three-dimensional distribution of irradiation light amounts in an inner region of the object in the held state; and
a unit configured to acquire a three-dimensional image based on the photoacoustic image and the light amount distribution.

10. The apparatus according to claim 1, wherein the acquisition unit is configured to discriminate the contact region and a non-contact region where the object is not held by the holding member, based on the two-dimensional image.

11. The apparatus according to claim 1, wherein the estimation unit is configured to calculate the calculated contact region based on an estimation value of the three-dimensional shape.

12. The apparatus according to claim 1, wherein the estimation unit is configured to:
calculate an evaluation value based on a degree of matching between two-dimensional position information of the region obtained by projecting the calculated contact region onto the two-dimensional image and the two-dimensional position information of the contact region acquired by the acquisition unit, and
estimate the three-dimensional shape based on the evaluation value.

13. An image processing apparatus comprising:
an acquisition unit configured to acquire position information of a contact region between an object and a holding member based on an image obtained by imaging the object in a held state in which the object is held by the holding member; and
an estimation unit configured to estimate a three-dimensional shape of the object in the held state based on the position information of the contact region,
wherein the image includes a two-dimensional image,
wherein the acquisition unit is configured to acquire three-dimensional position information of the contact region from two-dimensional position information of the contact region in the two-dimensional image based on a shape of the holding member,
wherein the estimation unit is configured to estimate the three-dimensional shape such that three-dimensional position information of a calculated contact region contacting the holding member corresponds to the three-dimensional position information of the contact region acquired by the acquisition unit, and
wherein one or more of the acquisition unit or estimation unit are implemented by a processor and a memory.

14. The apparatus according to claim 13, further comprising a shape acquisition unit configured to acquire a three-dimensional shape model of the object before contact with the holding member, wherein the estimation unit is configured to estimate the three-dimensional shape of the object by deforming the shape model based on the position information of the contact region.

15. The apparatus according to claim 14, wherein the shape acquisition unit is configured to acquire the shape model based on a surface shape of the object which is obtained from a three-dimensional medical image of the object.

16. The apparatus according to claim 15, further comprising a unit configured to generate a deformed three-dimensional medical image by performing deformation processing for the three-dimensional medical image of the object so as to make the object have a shape estimated by the estimation unit.

17. The apparatus according to claim 13, wherein the holding member comprises a member being optically transmissive, and the image comprises an image obtained by imaging the object through the holding member.

18. The apparatus according to claim 13, wherein the acquisition unit is configured to extract information concerning the contact region based on a luminance value of an object depicted in the image.

19. The apparatus according to claim 13, further comprising:
a photoacoustic image acquisition unit configured to acquire a photoacoustic image obtained by imaging the object in the held state;
a medical image acquisition unit configured to acquire a medical image;
a unit configured to acquire a deformed medical image by deforming the medical image based on the three-dimensional shape estimated by the estimation unit; and
a unit configured to cause a display to display the photoacoustic image and the deformed medical image.

20. The apparatus according to claim 19, wherein the medical image acquisition unit is configured to acquire an MRI image as the medical image.

21. The apparatus according to claim 13, further comprising:
a photoacoustic image acquisition unit configured to acquire a photoacoustic image obtained by imaging the object in the held state;
a light amount distribution acquisition unit configured to acquire a light amount distribution based on the three-dimensional shape estimated by the estimation unit, the light amount distribution being a three-dimensional distribution of irradiation light amounts in an inner region of the object in the held state; and
a unit configured to acquire a three-dimensional image based on the photoacoustic image and the light amount distribution.

22. The apparatus according to claim 13, wherein the acquisition unit is configured to discriminate the contact region and a non-contact region where the object is not held by the holding member, based on the two-dimensional image.

23. The apparatus according to claim 13, wherein the estimation unit is configured to calculate the calculated contact region based on an estimation value of the three-dimensional shape.

24. The apparatus according to claim 13, wherein the estimation unit is configured to:
calculate an evaluation value based on a degree of matching between three-dimensional position information of the calculated contact region and the three-dimensional position information of the contact region acquired by the acquisition unit, and
estimate the three-dimensional shape based on the evaluation value.

25. An image processing method comprising:
acquiring position information of a contact region between an object and a holding member based on an image obtained by imaging the object in a held state in which the object is held by the holding member; and
estimating a three-dimensional shape of the object in the held state based on the position information of the contact region,
wherein the image includes a two-dimensional image,
wherein the acquiring includes acquiring two-dimensional position information of the contact region in the two-dimensional image, and
wherein the estimating includes estimating the three-dimensional shape such that two-dimensional position information of a region obtained by projecting a calculated contact region contacting the holding member onto the two-dimensional image corresponds to the two-dimensional position information of the contact region.

26. A non-transitory computer-readable storage medium storing a computer program for causing a computer to function as:
acquiring position information of a contact region between an object and a holding member based on an image obtained by imaging the object in a held state in which the object is held by the holding member; and
estimating a three-dimensional shape of the object in the held state based on the position information of the contact region,
wherein the image includes a two-dimensional image,
wherein the acquiring includes acquiring two-dimensional position information of the contact region in the two-dimensional image, and
wherein the estimating includes estimating the three-dimensional shape such that two-dimensional position information of a region obtained by projecting a calculated contact region contacting the holding member onto the two-dimensional image corresponds to the two-dimensional position information of the contact region.

27. An image processing method comprising:
acquiring position information of a contact region between an object and a holding member based on an image obtained by imaging the object in a held state in which the object is held by the holding member; and
estimating a three-dimensional shape of the object in the held state based on the position information of the contact region,
wherein the image includes a two-dimensional image,
wherein the acquiring includes acquiring three-dimensional position information of the contact region from two-dimensional position information of the contact region in the two-dimensional image based on a shape of the holding member, and
wherein the estimating includes estimating the three-dimensional shape such that three-dimensional position information of a calculated contact region contacting the holding member corresponds to the three-dimensional position information of the contact region.

28. A non-transitory computer-readable storage medium storing a computer program for causing a computer to function by:
acquiring position information of a contact region between an object and a holding member based on an image obtained by imaging the object in a held state in which the object is held by the holding member; and
estimating a three-dimensional shape of the object in the held state based on the position information of the contact region, wherein the image includes a two-dimensional image,
wherein the acquiring includes acquiring three-dimensional position information of the contact region from two-dimensional position information of the contact region in the two-dimensional image based on a shape of the holding member, and
wherein the estimating includes estimating the three-dimensional shape such that three-dimensional position information of a calculated contact region contacting the holding member corresponds to the three-dimensional position information of the contact region.

* * * * *